(12) United States Patent
Bogosian et al.

(10) Patent No.: US 8,435,769 B2
(45) Date of Patent: May 7, 2013

(54) USE OF GLYPHOSATE TO PRODUCE SHIKIMIC ACID IN MICROORGANISMS

(75) Inventors: Gregg Bogosian, Clarkson Valley, MO (US); Julia P. Frantz (nee O'Neil), Glendale, MO (US)

(73) Assignee: Monsanto Technology LLC, St. Louis, MO (US)

( * ) Notice: Subject to any disclaimer, the term of this patent is extended or adjusted under 35 U.S.C. 154(b) by 647 days.

(21) Appl. No.: 12/595,631

(22) PCT Filed: Apr. 11, 2008

(86) PCT No.: PCT/US2008/060079
§ 371 (c)(1),
(2), (4) Date: Feb. 15, 2010

(87) PCT Pub. No.: WO2008/128076
PCT Pub. Date: Oct. 23, 2008

(65) Prior Publication Data
US 2011/0020885 A1    Jan. 27, 2011

Related U.S. Application Data

(60) Provisional application No. 60/923,475, filed on Apr. 13, 2007.

(51) Int. Cl.
| | |
|---|---|
| *C12P 7/42* | (2006.01) |
| *C12P 21/02* | (2006.01) |
| *A01N 57/18* | (2006.01) |
| *C07C 61/22* | (2006.01) |

(52) U.S. Cl.
USPC ........... 435/146; 435/69.1; 504/206; 562/510

(58) Field of Classification Search .................. 435/146, 435/69.1; 504/206; 562/510
See application file for complete search history.

(56) References Cited

U.S. PATENT DOCUMENTS

| | | | |
|---|---|---|---|
| 5,120,837 | A | 6/1992 | Fotheringham et al. |
| 5,168,056 | A | 12/1992 | Frost |
| 5,763,483 | A | 6/1998 | Bischofberger et al. |
| 5,776,736 | A | 7/1998 | Frost et al. |
| 5,866,601 | A | 2/1999 | Lew et al. |
| 5,952,375 | A | 9/1999 | Bischofberger et al. |

(Continued)

FOREIGN PATENT DOCUMENTS

| | | |
|---|---|---|
| EP | 0418840 A2 | 3/1991 |
| EP | 0976734 A2 | 2/2000 |

(Continued)

OTHER PUBLICATIONS

Abrecht, et al., "The Synthetic Development of the Anti-Influenza Neuraminidase Inhibitor Oseltamivir Phosphate (Tamiflu): A Challenge for Synthesis and Process Research," Chimia, 58(9): 621-629 (2004).

(Continued)

*Primary Examiner* — Rosanne Kosson
(74) *Attorney, Agent, or Firm* — Senniger Powers LLP; James E. Davis

(57) ABSTRACT

The present invention provides methods for producing shikimic acid. In particular the invention provides methods for producing and isolating shikimic acid from a microorganism. Additionally, the invention provides methods for synthesizing compounds such as oseltamivir and 6-fluoroshikimic acid using shikimic acid produced from microorganisms.

13 Claims, 2 Drawing Sheets

U.S. PATENT DOCUMENTS

| | | | |
|---|---|---|---|
| 6,180,373 B1* | 1/2001 | Wich et al. | 435/108 |
| 6,316,232 B1 | 11/2001 | Sprenger et al. | |
| 6,436,664 B1 | 8/2002 | Iomantas et al. | |
| 6,472,169 B1 | 10/2002 | Frost et al. | |
| 6,613,552 B1 | 9/2003 | Frost et al. | |
| 6,794,164 B2 | 9/2004 | Malmberg et al. | |
| 7,214,535 B2* | 5/2007 | Sun et al. | 435/419 |
| 2008/0058210 A1 | 3/2008 | Anderson | |

FOREIGN PATENT DOCUMENTS

| | | |
|---|---|---|
| EP | 0759917 B1 | 4/2000 |
| EP | 1092766 A1 | 4/2001 |
| EP | 0763127 B1 | 3/2005 |
| WO | 00/44923 A1 | 8/2000 |
| WO | 02/06203 A1 | 1/2002 |
| WO | 02/29078 A2 | 4/2002 |
| WO | 03/057655 A1 | 7/2003 |
| WO | 2007/035323 A1 | 3/2007 |
| WO | 2008/027570 A2 | 3/2008 |
| WO | 2008128076 A | 10/2008 |

OTHER PUBLICATIONS

Adachi et al., "High Shikimate Production from Quinate with Two Enzymatic Systems of Acetic Acid Bacteria", Biosci Biotechnol Biochem., 70(10): 2579-2582 (2006).

Amrhein, et al., "Biochemica Basis for Glyphosate-Tolerance in a Bacterium and a Plant Tissue Culture," FEBS Letters, 157(1): 191-196 (Jun. 1983).

Amrhein, et al., "The Site of Inhibition of the Shikimate Pathway by Glyphosate. II. Interference of Glyphosate with Chorismate Formation in Vivo and in Vitro," Plant Physiol. 66: 830-834 (1980).

Anderson, et al., "Analytical method for determination of shikimic acid: Shikimic acid proportional to glyphosate application rates," Commun. Soil. Sci. Plant Anal., 32(17&18): 2831-2840 (2001).

Armstrong, et al., "A 37×103 molecular weight plasmid-encoded protein is required for replication and copy number control in the plasmid pSC101 and its temperature-sensitive derivative pHS1," J. Mol. Biol., 175: 331-347 (1984).

Ausubel et al., "Current Protocols in Molecular Biology", Short Protocols in Molecular Biology, Third Edition: 4-1 to 4-4, John Wiley & Sons, Inc., New York (1995).

Baird, et al., "Introduction of a new broadspectrum postemergence herbicide class with utility of herbaceous perennial weed control," Proc. North Central Weed Control Conference, 26: 64-68 (1971).

Balbas, et al., "Plasmid vector pBR322 and its special-purpose derivatives—a review," Gene, 50: 3-40 (1986).

Bentley, et al., "Plasmid-encoded protein: the principal factor in the "metabolic burden" associated with recombinant bacteria," Biotech. and Bioeng., 35: 668-681 (1990).

Bolivar, et al., "Construction and characterization of new cloning vehicles. II. A multipurpose cloning system," Gene, 2(2): 95-113 (1977).

Bongaerts, et al., "Metabolic engineering for microbial production of aromatic amino acids and derived compounds," Metabolic Engineering, 3: 289-300 (2001).

Bornemann, et al., "*Escherichia coli* chorismate synthase catalyzes the conversion of (6S)-6-fluoro-5-enolpyruvylshikimate-3-phosphate to 6-fluorochorismate. Implications for the enzyme mechanism and the antimicrobial action of (6S)-6-fluoroshikimate," J. Biol. Chem., 270(39): 22811-22815 (1995).

Bradley, et al., "Star role for bacteria in controlling flu epidemic?" Nature Reviews Drug Discovery 4: 945-946 (2005).

Brown, et al., "Twists and turns: A tale of two shikimate-pathway enzymes," Biochem. Soc. Trans., 31: 543-547 (2003).

Buehring, et al., "Shikimic acid accumulation in field-grown corn (*Zea mays*) following stimulated glyphosate drift," Journal of Agricultural and Food Chemistry, 55: 819-824 (2007).

Chandran, et al., "Phosphoenolpyruvate availability and the biosynthesis of shikimic acid," Biotechnol. Prog., 19: 808-814 (2003).

Cleophax et al., "A Stereospecific Converstion of (−)-Methyl Tri-O-benzoylquinate to the Corresponding (−)-Methyl Shikimate," Angewandte Chemie International Edition, 10(9): 652-653 (1971).

Cleophax et al., "No. 558.—Voie d'acces facile aux derives de l'acide shikimique at epi-4-shikimique," Bulletine De La Societe Chimique De France 1973 No. 11: 2992-2995.

Dangschat et al., "Kurze Orginalmitteilungen," Die Naturwissenschaften, 26: 562-563 (1938).

Dangschat et al., "Configurational Relationships Between Naturally Occurring Cyclic Plant Acids and Glucose" Biochim Biophys Acta., 4(1-3): 199-204 (1950).

Davies, et al., "(6S)-6-fluoroshikimic acid, an antibacterial agent acting on the aromatic biosynthetic pathway," Antimicrob. Agents Chemother., 38(2): 403-406 (1994).

Davis, et al., "Aromatic biosynthesis. VII. Accumulation of two derivatives of shikimic acid by bacterial mutants," J. Bacteriol., 66:129-136 (1953).

De Clerq, E., "Strategies in the design of antiviral drugs," Nature Reviews/Drug Discovery, 1: 13-25 (2002).

Dell, et al., "Identification and removal of impediments to biocatalytic synthesis of aromatics from D-glucose: Rate-limiting enzymes in the common aromatic pathway of aromatic amino acid biosynthesis," J. Am. Chem. Soc. 115: 11581-11589 (1993).

Falck et al., "Enantiospecific Synthesis of D-myo-Inositol 1,4,5-Trisphosphate from (−)-Quinic Acid", Journal of Organic Chemistry, 54(25): 5851-5852 (1989).

Farina, et al., "Tamiflu: The Supply Problem," Angew. Chem. Int. Ed., 45: 7330-7334 (2006).

Federspiel, et al., "Industrial synthesis of the key precursor in the synthesis of the anti-influenza drug oseltamivir phosphate (Ro 64-0796/002, GS-4104-02): Ethyl (3R,4S,5S)-4,5-epoxy-3-(1-ethylpropoxy)-cyclohex-1-ene-1-carboxylate," Organic Process Research and Development, 3: 266-274 (1999).

Fischer, et al., "Comparative action of glyphosate as a trigger of energy drain in eubacteria," J. Bacteriol.,168(3): 1147-1154 (1986).

Franz et al. "Methods of Preparing Glyphosate," Glyphosate: A Unique Global Herbicide, American Chemical Society, Chapter 8, 233-262 (1997).

Fukuta, et al., "De novo synthesis of Tamiflu via a catalytic asymmetric ring-opening of meso-aziridines with TMSN3," J. Am. Chem. Soc., 128: 6312-6313 (2006).

Garner, et al., "Biosynthesis of Phenylalanine," Amino Acids: Biosynthesis and Genetic Regulation, 323-338, Hermann and Somerville, Eds., Addison-Wesley Publishing Co., Reading, MA.

Grossbard et al., "The Herbicide Glyphosate", Butterworths, London, 231-240 (1985).

Harring, et al., Accumulation of Shikimic Acid: A Technique for Screening Glyphosate Efficacy, J Agric. Food Chem., 46: 4406-4412 (1998).

Hasunuma, et al., "Replication of plasmid pSC101 in *Escherichia coli* K12: Requirement for dnaA function," Molec. Gen. Genet. 154: 225-230 (1977).

Henry, et al., "Shikimate accumulation in sunflower, wheat, and proso millet after glyphosate application," Weed Science, 55: 1-5 (2007).

Herrmann, K., "The Common Aromatic Biosynthetic Pathway," Amino Acids: Biosynthesis and Genetic Regulation, Hermann and Somerville, Eds., Addison-Wesley Publishing Co., Reading MA, 301-322 (1983).

Herrmann, K., "The Shikimate Pathway: Early Steps in the Biosynthesis of Aromatic Compounds," The Plant Cell, 7: 907-919 (1995).

Herrmann, K., "The shikimate pathway as an entry to aromatic secondary metabolism" Plant Physiol. 107: 7-12 (1995).

Herrmann, et al., "The Shikimate Pathway," Annual Review of Plant Physiology and Plant Molecular Biology, 50: 473-503 (1999).

Ikeda, M., "Amino Acid Production Process," Advances in Biochemical Engineering/Biotechnology, 79: 1-35 (2003).

Johansson, et al., "Transcriptome Analysis of a Shikimic Acid Producing Strain of *Escherichia coli* W3110 Grown Under Carbon- and Phosphate-Limited Conditions," J. Biotechnol., 126: 528-545 (2006).

Johansson, et al., "Shikimic Acid Production by a Modified Strain of *E. coli* (W3110.shik1) Under Phosphate-Limited and Carbon-Limited Conditions," Biotechnology and Bioengineering, 92: 541-552 (2005).

Kim, et al., "Influenza Neuraminidase Inhibitors Possessing a Novel Hydrophobic Interaction in the Enzyme Active Site: Design, Synthesis, and Structural Analysis of Carbocyclic Sialic Acid Analogues with Potent Anti-Influenza Activity," Journal of American Chemical Society, 119: 681-690 (1997).

Kim, et al., "Structure-Activity Relationship Studies of Novel Carbocyclic Influenza Neuraminidase Inhibitors," Journal of Medicinal Chemistry, 41: 2451-2460 (1998).

Knop, et al., "Hydroaromatic Equilibration During Biosynthesis of Shikimic Acid," J. Am. Chem. Soc. 123: 10173-10182 (2001).

Kramer, et al., "Metabolic engineering for microbial production of shikimic acid," Metabolic Engineering, 5: 277-283 (2003).

McConkey, G.A., "Targeting the shikimate pathway in the malaria parasite *Plasmodium falciparum*," Antimicrob. Agents Chemother., 43(1): 175-177 (1999).

Mueller, et al., "Shikimate accumulates in both glyphosate-sensitive and glyphosate-resistant horseweed (*Conyza canadensis* L. Cronq.)," J. Agric. Food Chem., 51: 680-684 (2003).

Nelms, et al., "Novel mutations in the pheA gene of *Escherichia coli* K-12 which result in highly feedback inhibition-resistant variants of chorismate mutase/prephenate dehydrogenase," Appl. Environ. Microbiol., 58(8): 2592-2598 (1992).

Payne, et al., "Isolation of shikimic acid from star aniseed," Journal Chemical Education, 82(4): 599-600 (Apr. 2005).

Pittard, A.J., "Biosynthesis of the Aromatic Amino Acids," *Escherichia coli* and Salmonella: Cellular and Molecular Biology, F. C. Neidhardt, American Society for Microbiology Press, Washington, 368-394 (1987).

Pittard, A.J., "Biosynthesis of the Aromatic Amino Acids," *Escherichia coli* and Salmonella: Cellular and Molecular Biology, F. C. Neidhardt, American Society for Microbiology Press, Washington, 458-484 (1996).

Pline, et al., "Tolerance and Accumulation of Shikimic Acid in Response to Glyphosate Applications in Glyphosate-Resistant and Nonglyphosate-Resistant Cotton (*Gossypium hirsutum* L.)," Journal of Agricultural and Food Chemistry, 50: 506-512 (2002).

Polen, et al., "The global gene expression response of *Escherichia coli* to L-phenylalanine," Journal of Biotechnology, 115: 221-237 (2005).

Rao et al., "Studies Directed Towards the Synthesis of Immunosuppressive Agent FK-506: Synthesis of the Entire Top-Half" Tetrahedron Letters, 32(4); 547-550 (Jan. 1991).

Roberts, et al., "Evidence for the shikimate pathway in apicomplexan parasites," Nature, 393: 801-805 (Jun. 1998).

Roberts, et al., "The shikimate pathway and its branches in apicomplexan parasites," J. Infect. Dis. 185(Suppl. 1): S25-S36 (2002).

Rohloff, et al., "Practical total synthesis of the anti-influenza drug GS-4104," J. Org. Chem., 63: 4545-4550 (1998).

Sadaka, et al., "Extraction of shikimic and quinic acids," Chem. Eng. Comm., 173: 91-102 (1999).

Starcevic, et al., "Enzymes of the shikimic acid pathway encoded in the genome of a basal metazoan, *Nematostella vectensis*, have microbial origins," Proc. Natl. Acad. Sci. 105(7): 2533-2537 (2008).

Steinrucken, et al., "The herbicide glyphosate is a potent inhibitor of 5-enolpyruvyl-shikimic acid-3-phosphate synthase," Biochem. Biophys. Res. Commun. 94(4): 1207-1212 (1980).

Steinrucken, et al., "5-enolpyruvylshikimate-3-phosphate synthase of *Klebsiella pneumoniae*. 2. Inhibition by glyphosate [N-(phosphonomethyl)glycine]," Eur. J. Biochem., 143: 351-357 (1984).

Tan, et al., "Synthesis and preliminary evaluation of a library of polycyclic small molecules for use in chemical genetic assays," J. Am. Chem. Soc., 121: 9073-9087 (1999).

Vogel, et al., "Acetylornithinase of *Escherichia coli*: Partial purification and some properties," J. Biol. Chem., 218: 97-106 (1956).

Wanner, B.R., "Phosphorus Assimilation and Control of the Phosphate Regulon," *Escherichia coli* and Salmonella: Cellular and Molecular Biology, F. C. Neidhardt, American Society for Microbiology Press, Washington, 1357-1381 (1996).

White et al., "The Synthesis and Absolute Configuration of Mycosporins. A Novel Application of the Staudinger Reaction" J. Am. Chem. Soc., 111(24): 8970-8972 (1989).

Yeung, et al., "A Short Enantioselective Pathway for the Synthesis of the Anti-Influenza Neuraminidase Inhibitor Oseltamivir from 1,3-Butadiene and Acrylic Acid,", J. Am. Chem. Soc., 128: 6310-6311 (2006).

Bresnahan, G.A., et al., "Glyphosate Applied Preharvest Induces Shikimic Acid Accumulation in Hard Red Spring Wheat (*Triticum aestivum*)," 2003, J Agric Food Chem, 51:4004-4007.

Kretzmer, K., et al., "Assay Comparison for Measuring Shikimate in Glyphosate-Treated Plant Species," 2007 North Central Weed Science Society Proceedings, 1 Pg.

Kruper, A., et al., "Facile and Economical Preparation of [14C]-Labelled Shikimic Acid," 1989, J Label Comp and Radiopharma, 28(6):713-718.

Stasiak, M.A., et al., "Alterations of Growth and Shikimic Acid Levels by Sublethal Glyphosate Applications on Pin Cherry and Trembling Aspen," 1991, Can J For Res, 21:1086-1090.

Tokhver, A.K., "Effect of Illumination Intensity and Light Quality on Accumulation of Shikimic Acid in Buckwheat Seedlings under the Influence of Glyphosate," 1990, Sov Plant Physiol, 37:542-546.

Velini, E.D., et al., "Glyphosate Applied at Low Doses Can Stimulate Plant Growth," 2008, Pest Manag Sci, 64:489-496.

International Search Report issued in PCT/US2008/080189, dated Apr. 3, 2009, 8 pages.

Written Opinion issued in PCT/US2008/080189, dated Apr. 3, 2009, 9 pages.

International Search Report issued in PCT/US2008/060079, dated Aug. 20, 2008, 7 pages.

Written Opinion issued in PCT/US2008/060079, dated Aug. 20, 2008, 7 pages.

\* cited by examiner

FIG. 1

```
phosphoenolpyruvate + erythrose-4-phosphate

| DAHP synthase (EC 4.1.2.15)
                | aroF, aroG, and aroH 3-deoxy-D-arabino-heptulosonate-7-phosphate (DAHP)

| 3-dehydroquinate synthase (EC 4.6.1.3)
                | aroB 3-dehydroquinate

| 3-dehyroquinate dehydratase (EC 4.2.1.10)
                | aroD 3-dehydroshikimate

| shikimate dehydrogenase (EC 1.1.1.25)
                | aroE shikimic acid

| shikimate kinase (EC 2.7.1.71)
                | aroK and aroL shikimate-3-phosphate

| EPSP synthase (EC 2.5.1.19)
                | aroA 5-enolpyruvoylshikimate-3-phosphate (EPSP)

| chorismate synthase (EC 4.6.1.4)
                | aroC chorismate

|
                | (multiple pathways)
                | tryptophan
             tyrosine
           phenylalanine
       para-hydroxybenzoic acid
        para-aminobenzoic acid
       2,3-dihydroxybenzoic acid
              folate
            ubiquinone
            menaquinone
           enterochelin
```

USE OF GLYPHOSATE TO PRODUCE SHIKIMIC ACID IN MICROORGANISMS

FIELD OF THE INVENTION

The instant invention relates generally to methods and compositions for producing shikimic acid. More specifically, it relates to various methods for improved production of shikimic acid by microorganisms and to the use of shikimic acid prepared by these methods as a reagent in the synthesis of other compounds.

BACKGROUND OF THE INVENTION

Shikimic acid (trihydroxy-1-cyclohexene-1-carboxylic acid; Chemical Abstracts Registry Number 138-59-0) is the key precursor compound for the synthetic manufacture of oseltamivir ((3R,4R,5S)-4-(acetyl-amino)-5-amino-3-(1-ethylpropoxy)-1-cyclohexene-1-carboxylic acid ethyl ester; Chemical Abstracts Registry Number 196618-13-0) (Rohloff et al., 1998; Federspiel et al., 1999). Oseltamivir, an orally active inhibitor of the essential neuraminidase of influenza virus, was discovered by scientists at Gilead Sciences Inc. of Foster City, Calif. (Kim et al., 1997; Kim et al., 1998; Abrecht et al., 2004; Bischofberger et al., U.S. Pat. No. 5,763,483; Lew et al., U.S. Pat. No. 5,866,601; Bischofberger et al., U.S. Pat. No. 5,952,375; Bischofberger et al., European Patent EP 0759917 B1; Bischofberger et al., European Patent EP 0976734 B1).

During influenza virus replication, new virus particles are bound to a sialic acid side-chain on the virus receptor protein. The mechanism of the viral neuraminidase is to cleave off this sialic acid and release the newly replicated virus particles. Oseltamivir is a sialic acid analog that inhibits this cleavage reaction by binding to the active site of the neuraminidase. These abortively infected cells are destroyed, stopping the spread of the virus within the host. Oseltamivir has potential use in influenza pandemics, including of "bird flu", in the form of the pharmaceutical TAMIFLU® (De Clercq, 2002; Bradley, 2005; Farina and Brown, 2006). The pharmaceutical TAMIFLU® is the phosphate salt of oseltamivir (Chemical Abstracts Registry Number 204255-11-8; also known as Roche compound Ro 64-0796/002 and Gilead Sciences compound GS-4104-02). TAMIFLU® was first marketed by Roche in October 1999 (Farina and Brown, 2006). However, the large-scale production of the drug has been limited by the low availability of the shikimic acid precursor material.

Shikimic acid is a scarce and expensive chemical substance, being obtained principally from the seeds of woody shrubs, namely the Chinese star anise shrub (*Illicium verum*) native to China, and the shikimi-no-ki shrub (*Illicium anisatum*, formerly called *Illicium religiosum*) from whence shikimic acid got its name, native to Japan (Haslam, 1974; Sadaka and Garcia, 1999; Payne and Edmonds, 2005). About 30 kilograms of star anise or shikimi-no-ki seeds are required to produce one kilogram of shikimic acid (Farina and Brown, 2006). However, this natural source is limited, and insufficient to meet worldwide demand for TAMIFLU® (Bradley, 2005).

1.3 grams of shikimic acid are required to manufacture the 10 doses of TAMIFLU® needed to treat one person (Bradley, 2005). To produce enough TAMIFLU® to treat 400 million people (a conservative estimate of the need in the event of an influenza pandemic) would require 520,000 kilograms of shikimic acid. Worldwide annual production of shikimic acid is currently only about 100,000 kilograms. Another estimate of the need for TAMIFLU® in the event of a severe influenza pandemic is 30 billion doses, requiring 39 million kilograms of shikimic acid (Bradley, 2005).

Two alternative approaches to resolving the problem of shikimic acid scarcity have been recently explored. The first is the production of shikimic acid by microorganisms by a fermentation-based process (Farina and Brown, 2006). The second is based on new chemical synthesis routes to oseltamivir phosphate that do not utilize scarce natural products as precursor compounds, but rather use inexpensive and widely available chemicals (Fukuta et al., 2006; Yeung et al., 2006). The chemical routes that have been developed to date are functional only as academic, bench-scale syntheses, and are not efficient industrial processes that could compete with the current shikimic acid-based manufacturing process for oseltamivir phosphate (Farina and Brown, 2006).

To understand the fermentation-based processes, it would be useful to briefly review the biosynthetic pathway to shikimic acid. This pathway is known both as the common aromatic biosynthetic pathway (Herrmann, 1983; Pittard, 1987; Pittard, 1996) because it leads to (among other things) the aromatic amino acids, and also as the shikimate pathway (Haslam, 1974) after the metabolic intermediate in the pathway that was identified first. Several entire books and comprehensive review articles have been devoted to this important metabolic pathway (Haslam, 1974; Weiss and Edwards, 1980; Herrmann, 1983; Conn, 1986; Pittard, 1987; Haslam, 1993; Herrmann, 1995a; Herrmann, 1995b; Pittard, 1996; Herrmann and Weaver, 1999; Bongaerts et al., 2001; Kramer et al., 2003).

The common aromatic biosynthetic pathway is present in plants, bacteria, fungi, and other eukaryotic microorganisms. A search of on-line databases by the Applicants, specifically PubMed and the National Center for Biotechnology Information (NCBI), indicated that in addition to plants, bacteria, and fungi, the pathway is present in Stramenopiles such as brown algae and diatoms, Alveolata (within the Protista kingdom) such as ciliates, dinoflagellates and apicomplexa parasites, and various Euglenozoa. The common aromatic biosynthetic pathway is not found in most higher animals, such as nematodes, insects and other arthropods, mollusks, and vertebrates and other chordates including fishes, amphibians, reptiles, birds and mammals. It has been established by others that the common aromatic biosynthetic pathway is present in the parasitic protozoan microorganisms known as apicomplexa (Roberts et al., 1998; McConkey, 1999; Roberts et al., 2002). It has also been suggested by others that the common aromatic biosynthetic pathway may be present in some higher animals, specifically in basal metazoans among the marine and freshwater invertebrates known as cnidarians (or coelenterates), including corals, sea anemones, jellyfishes, and hydroids (Starcevic et al., 2008). It is to be understood that statements that the common aromatic biosynthetic pathway is present in microorganisms mean that the pathway occurs in microscopic organisms and taxonomically related macroscopic organisms within the categories algae, Archaea, bacteria, fungi, and protozoa; this includes prokaryotes, including cyanobacteria, as well as unicellular eukaryotic organisms.

The facts that microorganisms possess the common aromatic biosynthetic pathway, and depend on it for the biosynthesis of many essential cellular components, and that mammals (including humans) lack the pathway, make the enzymes of the pathway attractive targets for new classes of antimicrobial therapeutic agents (Davies et al., 1994; Roberts et al., 1998). Any such therapeutic agents that are based on shikimic acid would increase the demand for shikimic acid. Indeed, 6-fluoroshikimic acid has been found to be an effective antibacterial compound (Davies et al., 1994; Bornemann et al., 1995) and anti-parasitical compound (McConkey, 1999; Roberts et al., 2002). Shikimic acid has also been converted into compounds that exhibited a significant inhibitory effect on cell proliferation, opening their possible use as anti-cancer chemotherapeutic agents (Tan et al., 1999). Thus, shikimic acid could serve as an important building block for a wide array of important classes of drugs, including anti-viral, anti-bacterial, anti-parasitical, and anti-cancer drugs.

In the bacterium *Escherichia coli*, the first step in the common aromatic biosynthetic pathway (FIG. 1) is carried out by three isofunctional DAHP synthase enzymes; these three isofunctional enzymes are encoded by the aroF, aroG, and aroH genes. Similarly, there are two isofunctional enzymes of shikimate kinase, encoded by the aroK and aroL genes. The other enzymes of the pathway consist of single enzymes and are encoded by single genes: the aroB gene encodes 3-dehydroquinate synthase, the aroD gene encodes 3-dehydroquinate dehydratase, the aroE gene encodes shikimate dehydrogenase, the aroA gene encodes EPSP synthase, and the aroC gene encodes chorismate synthase.

A fermentation-based route to shikimic acid was described by John W. Frost and co-workers at Michigan State University who reported construction of a strain of *E. coli* with several genetic modifications that led to the production of shikimic acid (Draths et al., 1999; Frost et al., International Publication No. WO 00/44923; Frost et al., International Publication No. WO 02/29078; Frost et al., U.S. Pat. No. 6,472,169; Frost et al., U.S. Pat. No. 6,613,552). These modifications included adding a second copy of the aroB gene, encoding 3-dehydroquinate synthase, to the chromosome of the host cell. In addition, a mutant form of the aroF gene, encoding a feedback-resistant DAHP synthase enzyme, and a wild-type copy of the aroE gene, encoding shikimate dehydrogenase, were placed on a multicopy plasmid in the host cell. These genetic modifications increased the flow of metabolites to shikimic acid. Finally, these workers described genetically disabling ("knocking out") the aroK and aroL genes encoding the two isofunctional shikimate kinase enzymes. Such a disabled strain would be, in theory, completely blocked in the conversion of shikimic acid to shikimate-3-phosphate (FIG. 1) and would accumulate shikimic acid.

Early on, it was reported that a mutant with such a block in the pathway would accumulate shikimic acid (Davis and Mingioli, 1953). However, such a disabled strain would also be unable to make the aromatic amino acids tryptophan, phenylalanine, and tyrosine, as well as the other essential compounds para-hydroxybenzoic acid, para-aminobenzoic acid, and 2,3-dihydroxybenzoic acid (FIG. 1). Indeed, in order to grow this strain in a fermenter, the fermentation medium had to be supplemented with all six of these essential compounds, specifically tryptophan (350 milligrams per liter), phenylalanine (700 milligrams per liter), tyrosine (700 milligrams per liter), para-hydroxybenzoic acid (10 milligrams per liter), para-aminobenzoic acid (10 milligrams per liter), and 2,3-dihydroxybenzoic acid (10 milligrams per liter) (see, for example, Draths et al., 1999, in supplementary materials published on-line; Frost et al., International Publication No. WO 00/44923, page 13, lines 24-30; Frost et al., International Publication No. WO 02/29078, page 28, lines 5-11; Frost et al., U.S. Pat. No. 6,472,169, column 16, lines 23-33; and Frost et al., U.S. Pat. No. 6,613,552, column 10, lines 23-33). The levels of shikimic acid in fermentation cultures of this strain ranged from 20 to 50 grams per liter. Further work with this strain by Frost and colleagues has improved the yield of shikimic acid to up to 80-90 grams per liter (Knop et al., 2001; Bongaerts et al., 2001; Chandran et al., 2003; Kramer et al., 2003). A nearly identical approach has been reported by workers in Sweden (Johansson et al., 2005; Johansson and Liden, 2006; Johansson, 2006).

A similar approach was reported by workers in Russia (Iomantas et al., U.S. Pat. No. 6,436,664) who used mutant strains of the bacterial genus *Bacillus* that were deficient in shikimate kinase to produce shikimic acid by fermentation. The fermentation medium, as necessitated by such mutants, had to be supplemented with the required compounds (see column 5, lines 38-52 of the patent). The levels of shikimic acid in fermentation cultures of these strains ranged from 3 to 17 grams per liter. Workers in Japan (Shirai et al., European Patent Application EP 1092766 A1) reported a similar approach with mutant strains of the bacterial genus *Citrobacter* to produce shikimic acid by fermentation. Again, the fermentation medium had to be supplemented with the required compounds (see, for example, Tables 3 and 4 of the patent application). The levels of shikimic acid in fermentation cultures of these strains ranged from 4 to 10 grams per liter. These various approaches have been the subject of review articles by Bongaerts et al. (2001) and Kramer et al. (2003). Methods have been developed for the recovery of shikimic acid from fermentation cultures (Malmberg and Westrup, U.S. Pat. No. 6,794,164; Van der Does et al., International Publication No. WO 02/06203).

All previous fermentation-based processes for the production of shikimic acid discussed here employ fermentation culture media containing expensive nutrient components such as tryptophan, phenylalanine, tyrosine, para-hydroxybenzoic acid, para-aminobenzoic acid, and 2,3-dihydroxybenzoic acid, or other expensive nutrient components. The cost of these nutrient component additions is considerable. The addition of tryptophan, phenylalanine, tyrosine, para-hydroxybenzoic acid, para-aminobenzoic acid, and 2,3-dihydroxybenzoic acid at the levels disclosed in the papers, patents, and patent applications discussed above (Draths et al., 1999; Frost et al., International Publication No. WO 00/44923; Frost et al., International Publication No. WO 02/29078; Frost et al., U.S. Pat. No. 6,472,169; Frost et al., U.S. Pat. No. 6,613,552) would increase the cost of the culture medium by about one dollar per liter (in 2007 US dollars).

Additionally to produce 39 million kilograms of shikimic acid per year by a fermentation process yielding 80 grams of shikimic acid per liter, and also requiring the amounts of the nutrient components reported in the cited papers, patents, and patent applications, would require (each year) about 340 metric tons each of tyrosine and phenylalanine, about 170 metric tons of tryptophan, and about 490 kilograms each of para-hydroxybenzoic acid, para-aminobenzoic acid, and 2,3-dihydroxybenzoic acid. As one example of the limitations imposed by the worldwide supply of these nutrients, the entire yearly global production of tyrosine is about 120 metric tons per year (Ikeda, 2003), far short of the 340 metric tons of tyrosine needed to produce 39 million kilograms of shikimic acid by the cited fermentation processes. In contrast, the cost of using the chemically defined minimal culture medium described in the instant invention (including the addition of glyphosate) would cost about 100-fold less, and at the most would consume about 3700 metric tons of glyphosate, which is only about 0.8% of the yearly global production of about 460,000 metric tons of glyphosate (N-(phosphonomethyl)-glycine; Chemical Abstracts Registry Number 1071-83-6). Glyphosate, inter alia, is an inhibitor of the enzyme 5-enolpyruvoylshikimate-3-phosphate synthase (EPSP synthase), and it therefore inhibits the common aromatic biosynthetic pathway at the point of conversion of shikimate-3-phosphate by the enzyme EPSP synthase to EPSP (FIG. 1). Inhibition of EPSP synthase by glyphosate may lead to the accumulation of shikimate-3-phosphate in the cell.

Anderson et al. (2001) disclose a method for the determination of shikimic acid in plant tissue after exposure of the plant to glyphosate. Shikimic acid analysis of the plant tissue was performed using water extraction followed by high-pressure liquid chromatography (HPLC) analysis.

SUMMARY OF THE INVENTION

It is clear that a more efficient method of producing shikimic acid is needed. One object of the instant invention to provide a process for the production of shikimic acid that employs a simple and inexpensive fermentation culture medium, one solely composed of an inexpensive chemically defined minimal culture medium and an inexpensive and readily available carbon source. Further objects of the invention include methods and strains that produce shikimic acid using this fermentation-based process. The accomplishment of these objectives will be understood and appreciated by the skilled artisan by referring to the following description of the invention and its claims.

Various embodiments of the instant invention provide methods for producing shikimic acid. Various aspects of these embodiments of the invention provide for the production of shikimic acid from *Escherichia coli* (*E. coli*) cultures. Aspects of this embodiment provide methods that comprise the steps of providing a culture of a microorganism; where the microorganism is capable of producing shikimic acid (typically by converting shikimate-3-phosphate to shikimic acid. The various aspects of this embodiment of the invention further comprise contacting the microorganism with glyphosate and then isolating shikimic acid from the culture.

Other embodiments of the invention provide methods for producing shikimic acid from a microorganism by employing steps comprising: (a) deregulating the microorganism's common biosynthetic pathway; (b) exposing the microorganism to glyphosate to increase the biosynthesis of shikimate-3-phosphate; (c) converting the shikimate-3-phosphate to shikimic acid.

Other embodiments of the invention provide methods for synthesizing chemical compounds using shikimic acid as a reagent, where the shikimic acid used has been prepared using one or more of the methods of the current invention for producing shikimic acid.

BRIEF DESCRIPTION OF THE DRAWINGS

The following figures form part of the present specification and are included to further demonstrate certain aspects of the present invention. The invention may be better understood by reference to one or more of these figures in combination with the detailed description of specific embodiments presented herein.

FIG. 1: The common aromatic biosynthetic pathway, also known as the shikimate pathway. The first step is the conversion of the central metabolites phosphoenolpyruvate and erythrose-4-phosphate into 3-deoxy-D-arabino-heptulosonate-7-phosphate (DAHP). Three more steps in the pathway yield shikimic acid, which in turn is converted in three additional steps to chorismic acid. Chorismic acid is a key intermediate in the biosynthesis of the aromatic amino acids tryptophan, phenylalanine, and tyrosine, as well as the other essential compounds para-hydroxybenzoic acid, para-aminobenzoic acid, 2,3-dihydroxybenzoic acid, and other compounds such as folate, ubiquinone, menaquinone, and enterochelin. In *Escherichia coli*, the first step in the common aromatic biosynthetic pathway is carried out by three isofunctional DAHP synthase enzymes; these three isofunctional enzymes are encoded by the aroF, aroG, and aroH genes. Similarly, there are two isofunctional enzymes of shikimate kinase, encoded by the aroK and aroL genes. The other enzymes of the pathway consist of single enzymes and are encoded by single genes: the aroB gene encodes 3-dehydroquinate synthase, the aroD gene encodes 3-dehydroquinate dehydratase, the aroE gene encodes shikimate dehydrogenase, the aroA gene encodes EPSP synthase, and the aroC gene encodes chorismate synthase.

DESCRIPTION OF THE SEQUENCE LISTING

Figure 2:
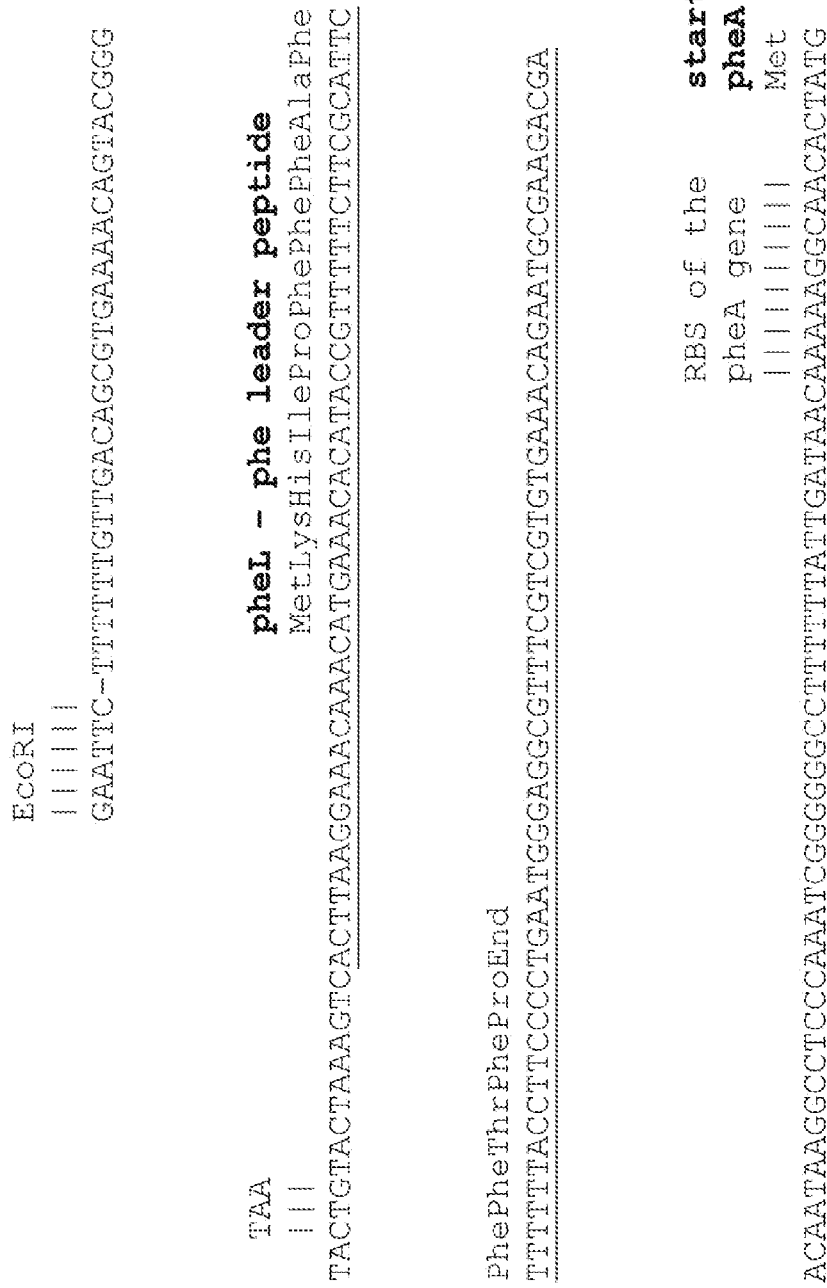
FIG. 2: Alterations to the promoter region of the *E. coli* pheA gene carried on pXT1457 and pXT1483. Two regions were altered in the promoter region. A promoter-up mutation was introduced in the −10 region of the pheA promoter, changing it from TACTGTA to TATAATA. Also, a 146 bp deletion was introduced between the pheA promoter and the ribosome binding site (RBS) of the pheA gene, removing the pheA attenuator region including the pheL leader peptide gene. Underlined nucleotides represent those nucleotides that were deleted. The EcoRI restriction site was placed where indicated, immediately before the promoter region of the pheA gene. SEQ ID NO: 4 is the nucleotide sequence listed in FIG. 2, while SEQ ID NO: 5 is the amino acid sequence listed in FIG. 2.

SEQ ID NO: 1 Nucleotide sequence of the synthetic EcoRI-BamHI restriction fragment carried on the plasmids pXT1457 and pXT1483.

SEQ ID NO: 2 Amino acid sequence of the feedback-resistant *E. coli* chorismate mutase-prephenate dehydratase encoded on the plasmids pXT1457 and pXT1483.

SEQ ID NO: 3 Nucleotide sequence of the plasmid pXT1483.

SEQ ID NO: 4 Nucleotide sequence illustrating the alterations to the promoter region of the *E. coli* pheA gene carried on the pXT1457 and pXT1483 plasmids.

SEQ ID NO: 5 Amino acid sequence encoded by a portion of the deleted pheL leader peptide gene.

Definitions

The following definitions are provided to facilitate those skilled in the art to fully understand and appreciate the scope of the present invention. As suggested in the definitions provided below, the definitions provided are not intended to be exclusive, unless so indicated. Rather, they are preferred definitions, provided to focus the skilled artisan on various illustrative embodiments of the invention.

As used herein, the term "derivative of shikimic acid" refers, without limitation, to any chemical compound that is prepared using shikimic acid and/or shikimate-3-phosphate as starting reagents.

As used herein, the term "microorganism" preferably refers to microscopic organisms and taxonomically related macroscopic organisms within the categories algae, Archaea, bacteria, fungi, Stramenopiles, Protista, and apicomplexa, that contain the common aromatic biosynthetic pathway, also known as the shikimate pathway. This definition includes all prokaryotes, including cyanobacteria and other bacteria, as well as all unicellular eukaryotic organisms, including Stramenopiles such as brown algae and diatoms, Alveolata (within the Protista kingdom) such as ciliates, dinoflagellates and apicomplexa parasites, and various Euglenozoa, that contain the common aromatic biosynthetic pathway.

As used herein, the term "minimal culture medium" preferably refers to a chemically defined culture medium. In such a culture medium, the chemical elements needed to support growth are provided by inorganic salts such as phosphates, sulfates, and the like. The carbon source is defined, and is usually a sugar such as glucose, lactose, galactose, and the like, or other compounds such as glycerol, lactate, acetate, and the like. While some such culture media also use phosphate salts as a buffer, other buffers may be employed such as citrate, triethanolamine, and the like.

As used herein, the terms "deregulate", "deregulation", "deregulated" and "deregulating" preferably refer to a deliberate increase of the flow of metabolites through a metabolic pathway, achieved by disabling one or more of the mechanisms that normally function to control such flow of metabolites. This deregulation may be achieved by disabling any of the mechanisms that repress the expression of any of the genes encoding any of the enzymes that carry out the steps of the metabolic pathway (referred to herein as "derepress" or "derepression" or "derepressed" or "derepressing"). This deregulation may also be achieved by rendering any of the enzymes, normally subject to feedback-inhibition by a metabolite in the pathway, resistant to such feedback-inhibition. Deregulation may also be achieved by any combination of derepression and feedback-inhibition mechanisms.

As used herein, the terms "optical density" and "OD" refer to an estimate of the concentration of cells of a microorganism suspended in a culture medium. Such optical density estimates are made spectrophotometrically and measure the decrease in transmitted light. Optical density is given by $\log_{10}(I_0/I)$, where $I_0$ is the intensity of the incident light, and I is the intensity of the transmitted light. For a given type of cell, the relationship between OD and cell concentration is linear over a wide range. As used herein, optical density measurements were made using light with a wavelength of 550 nanometers.

As used herein, the term "glyphosate" refers to N-(phosphonomethyl)glycine, a salt, ester or other derivative of N-(phosphonomethyl)glycine which is converted to glyphosate or which otherwise provides glyphosate anion. In this regard it is to be noted that the term "glyphosate" when used herein is understood to encompass N-(phosphonomethyl) glycine and such derivatives as well as mixtures thereof unless the context requires otherwise. Suitable salts of N-(phosphonomethyl)glycine include mono-, di- or tribasic forms and include organic ammonium, alkali metal, alkaline earth metal, ammonium (e.g., mono-, di- or triammonium) and sulfonium (e.g., mono-, di- or trimethylsulfonium) salts of N-(phosphonomethyl)glycine. The organic ammonium salts can comprise aliphatic or aromatic ammonium salts and can include primary, secondary, tertiary or quaternary ammonium salts. Specific representative examples of such organic ammonium salts include isopropylammonium, N-propylammonium, ethylammonium, dimethylammonium, 2-hydroxyethylammonium (also referred to as monoethanolammonium), ethylenediamine and hexamethylenediamine salts of N-(phosphonomethyl)glycine. Specific representative examples of alkali metal salts include potassium and sodium salts of N-(phosphonomethyl)glycine.

Description Of The Preferred Embodiments

Various embodiments of the present invention provide methods for producing shikimic acid wherein the method comprises: a) providing a microorganism culture; wherein the microorganism is capable of converting shikimate-3-phosphate to shikimic acid; b) contacting the microorganism with glyphosate; and c) converting shikimate-3-phosphate to shikimic acid. In preferred aspects of this embodiment the microorganism is *Escherichia coli* (*E. coli*). In more preferred aspects of this embodiment of the invention the microorganism is *E. coli* strain LBB427. In ever more preferred aspects of this embodiment of the invention the microorganism is *E. coli* strain LBB427 transformed with the plasmid pXT1457 or with the plasmid pXT1483.

In various aspects of this embodiment of the invention the conversion of shikimate-3-phosphate to shikimic acid may be accomplished by any suitable mechanism including but not limit to enzymatic methods, chemical methods, and/or physical methods (examples include, but are not limited to enzymatic conversion and heating in a low pH environment). In preferred aspects of this embodiment of the invention the conversion is through an enzymatic catalysis. In especially preferred aspects of this embodiment the enzymatic conversion is accomplished by a phosphatase, (e.g. an alkaline phosphatase). In all embodiments of the invention the conversion of shikimate-3-phosphate may take place either intra-cellularly or extra-cellularly. Moreover, the instant invention envisions the conversion step occurring either with or without the isolation of shikimate-3-phosphate. That is, various embodiments of the invention provide for the production of shikimate-3-phosphate by any of the methods described herein, purification of shikimate-3-phosphate and subsequent hydrolysis of shikimate-3-phosphate to shikimic acid by any suitable method known to those skilled in the art.

In another aspect of this embodiment of the invention, conversion of shikimate-3-phosphate to shikimic acid may be accomplished by physical means. It has been reported that shikimate-3-phosphate can be converted to shikimic acid by lowering the pH and/or raising the temperature of culture samples in which the microorganisms are grown. (Davis and Mingioli, 1953). Thus, in certain embodiments conversion of shikimate-3-phosphate to shikimic acid is accomplished by lowering the pH of the culture medium and/or increasing the temperature of the culture medium. These adjustments to the pH and/or temperature of the culture medium are made subsequent to the contact of the microorganism in the medium with glyphosate, and before recovery of the shikimic acid from the microorganism or medium. Generally, the pH of the medium may be lowered to below the typical cell culture growth pH of about 7, and preferably lowered to a pH of about 1. Generally, the temperature of the medium may be raised to a temperature greater than the typical cell culture growth temperature of about 37 degrees Celsius, and preferably to a temperature of at least about 60 degrees Celsius.

Other embodiments of the invention provide for methods of isolating shikimic acid, by purifying it after producing it by any of the methods described herein.

Other embodiments of the instant invention provide methods for producing shikimic acid from microorganisms where the method comprises: a) deregulating a microorganism's common aromatic biosynthetic pathway; b) contacting the microorganism with glyphosate; and c) converting shikimate-3-phosphate to shikimic acid. In preferred aspects of this embodiment of the invention the microorganism is *Escherichia coli* (*E. coli*). In more preferred aspects of this embodiment of the invention the microorganism is *E. coli* strain LBB427. In ever more preferred aspects of this embodiment of the invention the microorganism is *E. coli* strain LBB427 transformed with the plasmid pXT1457 or with the plasmid pXT1483. In any of the aspects of this embodiment of the invention the shikimate-3-phosphate may be converted to shikimic acid by any suitable method. Preferably, the conversion of shikimate-3-phosphate to shikimic acid is by a chemical, physical and/or enzymatic method. Preferably, the shikimate-3-phosphate is converted to shikimic acid by a phosphatase enzyme; more preferably by an alkaline phosphatase enzyme.

Some aspects of this embodiment of the invention comprise deregulating the biosynthesis of one or more compound selected from the group consisting of tryptophan, phenylalanine, tyrosine, shikimic acid, shikimate-3-phosphate, 5-enolpyruvoylshikimate-3-phosphate, chorismic acid, para-hydroxybenzoic acid, para-aminobenzoic acid, 2,3-dihydroxybenzoic acid, folate, ubiquinone, menaquinone, and enterochelin. In preferred aspects of this embodiment of the invention the deregulation is carried out in a bacterium, preferably in E. coli.

In various embodiments of the invention the biosynthesis of phenylalanine is deregulated in a microorganism. In preferred aspects of this embodiment the microorganism is Escherichia coli (E. coli). In more preferred aspects of this embodiment of the invention the microorganism is E. coli strain LBB427. In ever more preferred aspects of this embodiment of the invention the microorganism is E. coli strain LBB427 transformed with the plasmid pXT1457 or with the plasmid pXT1483.

In various aspects of this embodiment the microorganism is contacted with glyphosate by adding it to the culture medium. The glyphosate may be used at any effective concentration. In preferred embodiments of the invention the glyphosate is added at a concentration of 1 millimolar or greater. In more preferred embodiments the glyphosate is added at a concentration of 10 millimolar or greater. In other preferred embodiments of the invention the glyphosate is added at a concentration of from about 10 millimolar to about 50 millimolar; more preferably, the glyphosate is added at a concentration of from about 20 millimolar to about 50 millimolar. In an especially preferred embodiment of the invention the glyphosate is added at a concentration of about 20 millimolar.

Shikimic acid and/or shikimate-3-phosphate is typically recovered from the culture medium or culture supernatant about 5 hours subsequent to the exposure of the medium or the microorganisms therein to glyphosate. Yield of shikimic acid and/or shikimic-3-phosphate may be optimized relative to the particular microorganism utilized by shortening or lengthening the period of time between glyphosate exposure and shikimic acid and/or shikimic-3-phosphate recovery. Shikimic acid and/or shikimate-3-phosphate concentration in the culture medium tends to increase for a period of time following glyphosate exposure and then plateaus. Adjustments to the time period based on the particular microorganism utilized to optimize recovery can be readily determined by one skilled in the art.

In preferred aspects of this embodiment of the invention the microorganism is grown in a minimal culture medium. The microorganism may be grown using any suitable method known to those of skill in the art. In preferred embodiments of the invention the microorganisms are produced using either a shaker flask or a fermentation based process (i.e. in a controlled bioreactor) wherein the microorganism is grown to an optical density (O.D.) of greater than two (2); preferably an O.D. of greater than 10, greater than 20, greater than 50, or greater than 100.

In any aspect of the instant invention the fermentation-based culture may be used to produce shikimic acid at a rate of greater than 1 gram/liter, preferably greater than about 20 grams/liter; more preferably, greater than about 40 grams/liter; greater than 90 grams/liter; or greater than 100 grams/liter.

In various aspects of the invention the microorganism may be algae, Archaea, bacteria, fungi, or protozoa; including prokaryotes, cyanobacteria, and unicellular eukaryotic organism.

Other embodiment of the invention provide methods for synthesizing a chemical compound, either in vitro or in vivo, wherein shikimic acid produced and/or isolated by one of the methods of the current invention is used as a reagent in the synthesis. In preferred, aspects of this embodiment of the invention the compound is bioactive and has activity as an anti-microbial agent and/or a cell proliferation inhibitory agent (including, but not limited to a bioactive property selected from the group consisting of: anti-bacterial activity, anti-viral activity, anti-parasitical activity). In preferred aspects of this embodiment of the invention the compound has anti-bacterial and/or anti-viral properties. In other aspects of this embodiment of the invention the synthesized compound is 6-fluoroshikimic acid or oseltamivir or oseltamivir phosphate prepared by any suitable method known to those skilled in the art.

EXAMPLES

The following examples are included to demonstrate preferred embodiments of the invention. It will be appreciated by those of skill in the art that the techniques disclosed in the following examples represent techniques discovered by the Applicants to function well in the practice of the invention, and thus can be considered to constitute preferred modes for its practice. However, those of skill in the art should, in light of the instant disclosure, also appreciate that many changes can be made in the specific embodiments that are disclosed, while still obtaining like or similar results, without departing from the scope of the invention. Thus, the examples are exemplary only and should not be construed to limit the invention in any way. To the extent necessary to enable and describe the instant invention, all references cited are herein incorporated by reference.

Example 1

Construction of a pBR322—Derived Plasmid Expressing an Unregulated pheA Gene Encoding a Chorismate Mutase-Prephenate Dehydratase Enzyme that is Resistant to Feedback-Inhibition by Phenylalanine A pheA gene with three alterations in the nucleotide sequence was prepared by DNA synthesis as an EcoRI-BamHI restriction fragment (SEQ ID NO: 1). The technique of DNA synthesis is known in the art (Khudyakov and Fields, 2003).

The three alterations were:
1. A promoter-up mutation in the −10 region of the pheA promoter, changing it from TACTGTA to TATAATA (FIG. 2)
2. A 146 bp deletion between the pheA promoter and the ribosome binding site (RBS) of the pheA gene, removing the pheA attenuator region including the pheL leader peptide gene (FIG. 2)
3. A 6 bp deletion spanning codons 304-305-306 of the pheA gene, altering the amino acid sequence of the encoded chorismate mutase-prephenate dehydratase from Ala-303, Thr-304, Gly-305, Gln-306, Gln-307 to Ala-Lys-Gln (SEQ ID NO:2). The nucleotide sequence (SEQ ID NO: 1) is changed from GCG-ACC-GGG- CAA-CAA to GCG-AAA-CAA; the 6 bp deletion is of the underlined nucleotides CC-GGG-C.

All three of these alterations to the nucleotide sequence of the pheA gene are known in the art (Nelms et al., 1992; Fotheringham and Nelms, U.S. Pat. No. 5,120,837; Fotheringham and Nelms, European Patent EP 0418840 B1). The change from TACTGTA to TATAATA (SEQ ID NO: 4) in the promoter region of the pheA gene (FIG. 2) increases the activity of this promoter. Removal of the pheA attenuator region including the pheL leader peptide gene (FIG. 2) leads to constitutive expression of the pheA gene, no longer subject to an attenuation mechanism of repression by phenylalanine (Pittard, 1996). The changes in the amino acid sequence of the altered chorismate mutase-prephenate dehydratase (SEQ ID NO:2) result in the enzyme being resistant to feedback-inhibition by phenylalanine.

This synthetic EcoRI-BamHI restriction fragment, carrying the altered pheA gene, was inserted into the standard cloning vector pBR322 (Bolivar et al, 1977; Pouwels et al., 1985; Balbas et al., 1986; Balbas et al., 1988) to yield the plasmid pXT1457. The techniques of manipulation of DNA molecules, including the cleavage of DNA molecules with restriction enzymes and the ligation of restriction fragments of DNA, are known in the art (Sambrook and Russell, 2001; Ausubel et al., 2005). While the plasmid pBR322 encodes resistance to both ampicillin and tetracycline, insertion of a DNA fragment between the EcoRI and BamHI sites of pBR322 disrupts the tetracycline resistance gene, and so pXT1457 encodes resistance only to ampicillin.

To confirm that the new plasmid was functioning as expected, the wild-type E. coli K-12 host strain LBB427 was transformed with the plasmid pXT1457. Techniques for transforming bacteria, including strains of E. coli, are known in the art (Sambrook and Russell, 2001; Ausubel et al., 2005). The shikimic acid and phenylalanine production levels of this strain were compared to that of the untransformed host strain LBB427. The strains were cultured in 50 milliliters of Vogel-Bonner minimal culture medium (Vogel and Bonner, 1956), consisting of magnesium sulfate heptahydrate ($MgSO_4$-$7H_2O$) at 298 milligrams per liter, anhydrous dibasic potassium phosphate ($K_2HPO_4$) at 14.93 grams per liter, sodium ammonium phosphate tetrahydrate ($NaNH_4HPO_4$-$4H_2O$) at 5.22 grams per liter, anhydrous citric acid (the free acid form) at 2.73 grams per liter, and glucose at 2.00 grams per liter. The pH of the culture medium was 7.0. For the strain LBB427 transformed with the plasmid pXT1457, ampicillin was included in the culture medium at 100 milligrams per liter. The cultures were grown in flasks, on an incubator shaker operating at 300 rpm and 37 degrees Celsius. At 24 hours after inoculation, the cells were pelleted by centrifugation, and the culture supernatants were analyzed by a high-pressure liquid chromatography (HPLC) assay for shikimic acid and phenylalanine content. To the samples to be assayed, phosphoric acid was added to a final concentration of 6 millimolar. The samples were injected onto a 0.5 centimeter by 200 centimeter Altec 5 micron Bondapak C-18 column, and the eluate was scanned from 190 to 300 nanometers.

Under these growth conditions, while the untransformed host strain LBB427 did not produce detectable levels of phenylalanine in the culture supernatant, the host strain LBB427 transformed with the plasmid pXT1457 did produce phenylalanine in the culture supernatant, at levels of about 400 milligrams of phenylalanine per optical density (OD) unit per liter.

Under these growth conditions, the untransformed host strain LBB427 did not produce detectable levels of shikimic acid in the culture supernatant. The host strain LBB427 transformed with the plasmid pXT1457 did produce shikimic acid in the culture supernatant, at levels of about 3 milligrams of shikimic acid per OD unit per liter.

These results confirmed that the presence of the altered pheA gene on the pBR322-derived plasmid pXT1457 transformed into the host strain LBB427 was leading to a deregulation of the common aromatic biosynthetic pathway in the strain.

Example 2

Construction of a pSC101-Derived Plasmid Expressing an Unregulated pheA Gene Encoding a Chorismate Mutase-Prephenate Dehydratase Enzyme that is Resistant to Feedback-Inhibition by Phenylalanine Plasmids derived from pBR322, such as pXT1457 described in Example 1, exist in an E. coli host cell at a copy number (the number of plasmid molecules per cell) of about 30; this copy number determination is described in Bogosian et al., International Publication No. WO 2007/035323 A1, which is hereby incorporated herein by reference in its entirety. To investigate the effect of the altered pheA gene when present on a lower copy number plasmid vector, a pSC101-derived cloning vector was constructed. The plasmid pSC101 has a copy number of about 15 (Hasunuma and Sekiguchi, 1977), which is intermediate between that of low copy number plasmids and high-copy number plasmids such as pBR322 (Armstrong et al., 1984).

The starting plasmid was the cloning vector pXT995. The plasmid pXT995 and its construction are described in Bogosian et al., International Publication No. WO 2007/035323 A1, which is hereby incorporated herein by reference in its entirety. The plasmid pXT995 is essentially the plasmid pBR322, with the only difference being that the pBR322-derived origin of replication on pXT995 is flanked by arrays of convenient restriction sites. At one end of the origin of replication, the array of restriction sites includes a site for the restriction enzyme NsiI, and at the other end of the origin of replication, the array of restriction sites includes a site for the restriction enzyme SacI. Thus, the origin of replication on the plasmid pXT995 can be excised by digestion of the plasmid with the enzymes NsiI and SacI, and replaced with an NsiI-SacI restriction fragment carrying a different origin of replication.

The origin of replication of the plasmid pSC101 was amplified by the polymerase chain reaction as an NsiI-SacI restriction fragment, and inserted into the plasmid pXT995. The technique of amplifying segments of DNA by the polymerase chain reaction is known in the art (Sambrook and Russell, 2001; Ausubel et al., 2005). This insertion replaced the NsiI-SacI fragment on pXT995 (that carried the pBR322-derived origin of replication) with the pSC101-derived origin of replication. The resulting plasmid was designated pXT1405. The plasmid pXT1405 is thus composed of the backbone of pBR322, including the genes encoding resistance to ampicillin and tetracycline, but with an origin of replication from pSC101.

This EcoRI-BamHI restriction fragment from pXT1457 (described in Example 1), carrying the altered pheA gene, was inserted into this new cloning vector pXT1405 to yield the plasmid pXT1483 (SEQ ID NO: 3). While the plasmid pXT1405 encodes resistance to both ampicillin and tetracycline, insertion of a DNA fragment between the EcoRI and BamHI sites of pXT1405 disrupts the tetracycline resistance gene, and so pXT1483 encodes resistance only to ampicillin.

Example 3

Treatment of Strains with Glyphosate

The untransformed host strain LBB427 and the host strain LBB427 transformed with the plasmid pXT1457 were grown in 50 milliliters of the Vogel-Bonner minimal culture medium described in Example 1. For the strain LBB427 transformed with the plasmid pXT1457, ampicillin was included in the culture medium at 100 milligrams per liter. The cultures were grown in flasks, on an incubator shaker operating at 300 rpm and 37 degrees Celsius. At 2.5 hours after inoculation, N-(phosphonomethyl)glycine was added to a concentration of 3.38 grams per liter (20 millimolar). Growth of the cultures was almost completely inhibited by this level of glyphosate. At 24 hours after inoculation (i.e., 21.5 hours after N-(phosphonomethyl)glycine addition), the cells were pelleted by centrifugation, and the culture supernatants were analyzed for shikimic acid content using the HPLC assay described in Example 1. The culture supernatants of the host strain LBB427 transformed with the plasmid pXT1457 were also analyzed for phenylalanine content.

Under these conditions of glyphosate treatment, the untransformed host strain LBB427 did not produce detectable levels of shikimic acid in the culture supernatant.

Under these same conditions of glyphosate treatment, the host strain LBB427 transformed with the plasmid pXT1457 also did not produce detectable levels of shikimic acid in the culture supernatant. This strain did produce phenylalanine in the culture supernatant, but only at levels of about 50 milligrams of phenylalanine per OD unit per liter.

These results indicated that the inhibition of the enzyme EPSP synthase by glyphosate inhibited the growth of both the transformed and untransformed strains, and reduced the biosynthesis of phenylalanine by the strain LBB427 transformed with the plasmid pXT1457. The fact that both the transformed and the untransformed strains did not produce detectable levels of shikimic acid indicated that the inhibition of the enzyme EPSP synthase by glyphosate was causing shikimate-3-phosphate to accumulate rather than shikimic acid.

Example 4

Growth of Strains Under Phosphate-Limiting Conditions

A phosphate-limiting culture medium was developed by the Applicants, containing anhydrous magnesium sulfate ($MgSO_4$) at 192 milligrams per liter, ammonium chloride ($NH_4Cl$) at 5.35 grams per liter, potassium chloride (KCl) at 3.73 grams per liter, sodium chloride (NaCl) at 1.17 grams per liter, triethanolamine (a buffering compound) at 22.3 grams per liter, and glucose at 1.5 grams per liter. The pH of the culture medium was 7.0. This culture medium does not contain any source of phosphate. This culture medium was designated PF culture medium (standing for phosphate-free culture medium). However, a phosphate-limiting medium may be formulated for use in the present invention such that, while not phosphate-free, it contains minimal amounts of phosphate (i.e., is substantially free of phosphate). Such a medium will create the phosphate-limiting conditions that result in a yield of shikimic acid in the cultured microorganisms that is comparable to the yield achieved when using a phosphate-free medium and that is greater than the yield achieved when using a typical phosphate containing medium such as the Vogel-Bonner minimal culture medium disclosed in Example 1. Generally, such a phosphate-limiting medium should contain phosphate at levels no more than about 1 millimolar, and preferably at levels no more than about 100 micromolar.

For pre-growth of the strains, sources of phosphate were supplied to this culture medium in the form of Casamino acids at 2.2 grams per liter and yeast extract at 300 milligrams per liter. This culture medium was designated PF-CAA/YE culture medium (standing for PF culture medium plus Casamino acids and yeast extract).

The untransformed host strain LBB427 and the host strain LBB427 transformed with the plasmid pXT1457 were grown initially in 50 milliliters of the PF-CAA/YE culture medium. For the strain LBB427 transformed with the plasmid pXT1457, ampicillin was included in the culture medium at 100 milligrams per liter. The cultures were grown for 2.5 hours in flasks, on an incubator shaker operating at 300 rpm and 37 degrees Celsius. The cells in these cultures were pelleted by centrifugation and resuspended in the same volume of the PF culture medium. For the strain LBB427 transformed with the plasmid pXT1457, ampicillin was included in the culture medium at 100 milligrams per liter. Upon return to the incubator shaker, the strains exhibited very little additional growth, confirming that they were phosphate-limited. The small amount of additional growth that was observed was presumably due to carry-over of small amounts of phosphate, most likely in the form of phosphate reserves inside the cells themselves. At 24 hours after inoculation, the cells were pelleted by centrifugation, and the culture supernatants were analyzed for shikimic acid content using the HPLC assay described in Example 1. The culture supernatants of the host strain LBB427 transformed with the plasmid pXT1457 were also analyzed for phenylalanine content.

Under these conditions of phosphate limitation, the untransformed host strain LBB427 did not produce detectable levels of shikimic acid in the culture supernatant. Under these same conditions of phosphate limitation, the host strain LBB427 transformed with the plasmid pXT1457 also did not produce detectable levels of shikimic acid in the culture supernatant. This strain did produce phenylalanine in the culture supernatant, at levels of about 500 milligrams of phenylalanine per OD unit per liter.

These results indicated that phosphate limitation of either the transformed or the untransformed strains did not lead to production of shikimic acid.

Example 5

Growth of Strains Under Phosphate-Limiting Conditions Combined With Treatment with Glyphosate The untransformed host strain LBB427 and the host strain LBB427 transformed with the plasmid pXT1457 or with the plasmid pXT1483 were grown initially in 50 milliliters of the PF-CAA/YE culture medium described in Example 4. For the strains of LBB427 transformed with the plasmid pXT1457 or with the plasmid pXT1483, ampicillin was included in the culture medium at 100 milligrams per liter. The cultures were grown for 2.5 hours in flasks, on an incubator shaker operating at 300 rpm and 37 degrees Celsius. The cells in these cultures were pelleted by centrifugation and resuspended in the same volume of the PF culture medium described in Example 4. For the strains of LBB427 transformed with the plasmid pXT1457 or with the plasmid pXT1483, ampicillin was included in the culture medium at 100 milligrams per liter. To these resuspended cultures, N-(phosphonomethyl) glycine was added to a concentration of 3.38 grams per liter (20 millimolar). Upon return to the incubator shaker, the strains exhibited very little additional growth. At 24 hours after inoculation (i.e., 21.5 hours after N-(phosphonomethyl) glycine addition), the cells were pelleted by centrifugation, and the culture supernatants were analyzed for shikimic acid content using the HPLC assay described in Example 1.

Under these conditions of glyphosate treatment and phosphate-limitation, the untransformed host strain LBB427 produced shikimic acid in the culture supernatant at levels of about 200 milligrams of shikimic acid per OD unit per liter. The host strain LBB427 transformed with the plasmid pXT1457 produced shikimic acid in the culture supernatant at levels of about 250 milligrams of shikimic acid per OD unit per liter. The host strain LBB427 transformed with the plasmid pXT1483 produced shikimic acid in the culture supernatant at levels of about 400 milligrams of shikimic acid per OD unit per liter.

It is possible that not all of the accumulated shikimate-3-phosphate in these cells had been converted into shikimic acid and excreted into the culture medium. As noted above, it has been reported that shikimate-3-phosphate can be converted to shikimic acid by lowering the pH and/or raising the temperature of culture samples (Davis and Mingioli, 1953). A sample of the culture of the host strain LBB427 transformed with the plasmid pXT1483 (taken at 24 hours after inoculation), including the cells, was adjusted to pH 1.0 with sulfuric acid, and heated to 60 degrees Celsius for 15 minutes. The cells were pelleted by centrifugation, and the culture supernatant was analyzed for shikimic acid content using the HPLC assay described in Example 1. The level of shikimic acid was found to be about 600 milligrams per OD unit per liter.

These results indicated that with the untransformed host strain LBB427, the inhibition of the enzyme EPSP synthase by glyphosate, combined with induction of the enzyme alkaline phosphatase by phosphate limitation, caused the strain to produce and excrete into the culture medium substantial quantities of shikimic acid.

These results further demonstrated that with the host strain LBB427 transformed with the plasmid pXT1457 or with the plasmid pXT1483, the combination of deregulation of the common aromatic biosynthetic pathway, glyphosate inhibition of the enzyme EPSP synthase, and induction of the enzyme alkaline phosphatase by phosphate limitation, caused the strain to produce and excrete into the culture medium even higher quantities of shikimic acid. Additional shikimic acid could be recovered from these cells by lowering the pH and raising the temperature of culture samples.

While not wishing to be bound by theory, the higher yield of shikimic acid obtained with the host strain LBB427 transformed with the plasmid pXT1483, compared to the host strain LBB427 transformed with the plasmid pXT1457, is possibly due to the lower plasmid copy number of pXT1483. The metabolic burden on cells to maintain multicopy plasmids is significant (Bentley et al., 1990), and could affect the capacity of the cell to produce compounds such as shikimic acid.

Example 6

Production of Shikimic Acid from a High-Density Fermentation Culture

The host strain LBB427 transformed with the plasmid pXT1483 can be grown to high optical densities in a phosphate-limited fermentation culture. Fermentations are conducted in a chemically-defined minimal medium containing 5.9 grams of anhydrous ammonium sulfate (($NH_4$)$_2SO_4$), 1.8 grams of anhydrous dibasic potassium phosphate ($K_2HPO_4$), 1.0 grams of monobasic sodium phosphate monohydrate ($NaH_2PO_4$—$H_2O$), 550 milligrams of magnesium sulfate heptahydrate ($MgSO_4$-$7H_2O$), 27 milligrams of ferric chloride hexahydrate ($FeCl_3$-$6H_2O$), 0.5 milligrams of zinc sulfate heptahydrate ($ZnSO_4$-$7H_2O$), 0.9 milligrams of cobalt chloride hexahydrate ($CoCl_2$-$6H_2O$), 0.9 milligrams of sodium molybdate dihydrate ($Na_2MoO_4$-$2H_2O$), 1.1 milligrams of cupric sulfate pentahydrate ($CuSO_4$-$5H_2O$), 0.3 milligrams of boric acid ($H_3BO_3$), and 0.7 milligrams of manganese sulfate monohydrate ($MnSO_4$—$H_2O$) per liter of water. The fermenter is maintained at 37 degrees Celsius. The pH is maintained at 7.0 by the controlled addition of concentrated (about 29%) ammonium hydroxide ($NH_4OH$). Glucose is fed at a controlled rate from a 50% stock solution to maintain a glucose concentration of 0.2%.

In the presence of excess phosphate, such fermentation cultures can be grown to optical densities in excess of 50 or even higher. In this phosphate-limited fermentation culture medium, the onset of phosphate starvation is apparent when the growth of the culture stops at lower optical densities. The addition of a small amount of additional phosphate, fed from a stock solution of 85% phosphoric acid ($H_3PO_4$), would allow the strain to grow to a higher optical density. When the culture reaches an optical density of about 20-40, and phosphate starvation has been initiated, N-(phosphonomethyl) glycine is added to a final concentration of 3.38 grams per liter (20 millimolar).

Twelve hours after N-(phosphonomethyl)glycine addition, samples of the fermentation cultures are taken for analysis of shikimic acid levels. The samples, including the cells, are adjusted to pH 1.0 with sulfuric acid, and heated to 60 degrees Celsius for 15 minutes. The cells are pelleted by centrifugation, and the culture supernatants are analyzed for shikimic acid content using the HPLC assay described in Example 1.

At an optical density of 40, shikimic acid is produced in the culture supernatant at levels of about 24 grams of shikimic acid per liter.

Example 7

Recovery and Isolation/Purification of Shikimic Acid from Culture Medium

Shikimic acid was recovered from the culture medium of the untransformed host strain LBB427 and the host strain LBB427 transformed with the plasmid pXT1457 or with the plasmid pXT1483, grown under phosphate-limiting conditions and treated with N-(phosphonomethyl)glycine as described in Example 5.

The cells in the cultures were pelleted by centrifugation. The culture supernatants were passed through a 0.2 micrometer filter, placed into a flask, and most of the water was allowed to evaporate. This led to the formation of crystals in the flasks. The remaining culture supernatants were discarded, and the crystals were redissolved in 10 milliliters of distilled water. The solutions were placed into a test tube, and most of the water was allowed to evaporate. This led to the formation of crystals in the test tubes. The supernatants were discarded, and the crystals were dissolved in 5 milliliters of distilled water. The resulting solutions were submitted to analysis, using the HPLC assay described in Example 1, and all were found to be composed of shikimic acid with a purity of greater than 99%.

All of the compositions and/or methods and/or processes and/or apparatus disclosed and claimed herein can be made and executed without undue experimentation in light of the instant disclosure. While the compositions and methods of this invention have been described in terms of preferred embodiments, it will be apparent to those of skill in the art that variations may be applied to the compositions and/or methods and/or apparatus and/or processes and in the steps or in the sequence of steps of the methods described herein without departing from the concept and scope of the invention. More specifically, it will be apparent that certain agents that are chemically and/or physiologically related may be substituted for the agents described herein while the same or similar results would be achieved. All such similar substitutions and modifications apparent to those skilled in the art are deemed to be within the scope and concept of the invention. To the extent necessary to enable and describe the instant invention, all references cited are herein incorporated by reference.

References

The following references, to the extent that they provide exemplary procedural or other details supplementary to those set forth herein, are specifically incorporated herein by reference.

Abrecht, S., P. Harrington, H. Iding, M. Karpf, R. Trussardi, B. Wirz, and U. Zutter. 2004. The synthetic development of the anti-influenza neuraminidase inhibitor oseltamivir phosphate (Tamiflu): A challenge for synthesis and process research. Chimia 58: 621-629.

Amrhein, N., B. Deus, P. Gehrke, and H. C. Steinrucken. 1980. The site of inhibition of the shikimate pathway by glyphosate. II. Interference of glyphosate with chorismate formation in vivo and in vitro. Plant Physiol. 66: 830-834.

Amrhein, N., D. Johanning, J. Schab, and A. Schulz. 1983. Biochemical basis for glyphosate-tolerance in a bacterium and a plant tissue culture. FEBS Letters 157: 191-196.

Anderson, K. A., W. T. Cobb, and B. R. Loper. 2001. Analytical method for determination of shikimic acid: Shikimic acid proportional to glyphosate application rates. Commun. Soil. Sci. Plant Anal. 32: 2831-2840.

Armstrong, K. A., R. Acosta, E. Ledner, Y. Machida, M. Pancotto, M. McCormick, H. Ohtsubo, and E. Ohtsubo. 1984. A 37×103 molecular weight plasmid-encoded protein is required for replication and copy number control in the plasmid pSC101 and its temperature-sensitive derivative pHS1. J. Mol. Biol. 175: 331-347.

Ausubel, F. M., R. Brent, R. E. Kingston, D. D. Moore, J. G. Seidman, J. A. Smith, and K. Struhl. 2005. "Current protocols in molecular biology". John Wiley and Sons, New York.

Baird, D. D., R. P. Upchurch, W. B. Homesley, and J. E. Franz. 1971. Introduction of a new broadspectrum postemergence herbicide class with utility of herbaceous perennial weed control. Proc. North Central Weed Control Conf. 26: 64-68.

Balbas, P., X. Soberon, E. Merino, M. Zurita, H. Lomeli, F. Valle, N. Flores and F. Bolivar. 1986. Plasmid vector pBR322 and its special-purpose derivatives—a review. Gene 50: 3-40.

Balbas, P., X. Soberon, F. Bolivar, and R. L. Rodriguez. 1988. The plasmid pBR322. In Rodriguez, R. L., and D. T. Denhardt (ed.) "Vectors. A survey of molecular cloning vectors and their uses", pp 5-41. Butterworths, Boston, Mass.

Bentley, W. E., N. Mirjalili, D. C. Andersen, R. H. Davis and D. S. Kompala. 1990. Plasmid-encoded protein: the principal factor in the "metabolic burden" associated with recombinant bacteria. Biotech. and Bioeng. 35: 668-681.

Bischofberger, N. W., C. U. Kim, W. Lew, H. Liu, and M. A. Williams. Carbocyclic compounds. U.S. Pat. No. 5,763,483.

Bischofberger, N. W., C. U. Kim, W. Lew, H. Liu, and M. A. Williams. Compounds and methods for synthesis and therapy. U.S. Pat. No. 5,952,375.

Bischofberger, N. W., C. U. Kim, W. Lew, H. Liu, and M. A. Williams. Novel selective inhibitors of viral or bacterial neuraminidases. European Patent EP 0759917 B1.

Bischofberger, N. W., C. U. Kim, W. Lew, H. Liu, and M. A. Williams. Selective inhibitors of viral or bacterial neuraminidases. European Patent EP 0976734 B1.

Bogosian, G., J. P. O'Neil, and H. Q. Smith. Hybrid portable origin of replication plasmids. International Publication No. WO 2007/035323 A1.

Bolivar, F., R. L. Rodriguez, P. J. Greene, M. C. Betlach, H. L. Heyneker and H. W. Boyer. 1977. Construction and characterization of new cloning vehicles. II. A multipurpose cloning system. Gene 2: 95-113.

Bongaerts, J., M. Kramer, U. Muller, L. Raeven, and M. Wubbolts. 2001. Metabolic engineering for microbial production of aromatic amino acids and derived compounds. Metabolic Engineering 3: 289-300.

Bornemann, S., M. J. Ramjee, S. Balasubramanian, C. Abell, J. R. Coggins, D. J. Lowe, and R. N. F. Thorneley. 1995. *Escherichia coli* chorismate synthase catalyzes the conversion of (6S)-6-fluoro-5-enolpyruvylshikimate-3-phosphate to 6-fluorochorismate. Implications for the enzyme mechanism and the antimicrobial action of (6S)-6-fluoroshikimate. J. Biol. Chem. 270: 22811-22815.

Bradley, D. 2005. Star role for bacteria in controlling flu epidemic? Nature Reviews Drug Discovery 4: 945-946.

Brown, K. A., E. P. Carpenter, K. A. Watson, J. R. Coggins, A. R. Hawkins, M. H. J. Koch, and D. I. Svergun. 2003. Twists and turns: A tale of two shikimate-pathway enzymes. Biochem. Soc. Trans. 31: 543-547.

Buehring, N. W., J. H. Massey, and D. B. Reynolds. 2007. Shikimic acid accumulation in field-grown corn (Zea mays) following stimulated glyphosate drift. J. Agric. Food Chem. 55: 819-824.

Casali, N., and A. Preston. 2003. *"E. coli* plasmid vectors. Methods and applications". Humana Press, Totowa, N.J.

Chandran, S. S., J. Yi, K. M. Draths, R. von Daeniken, W. Weber, and J. W. Frost. 2003. Phosphoenolpyruvate availability and the biosynthesis of shikimic acid. Biotechnol. Prog. 19: 808-814.

Conn, E. E. 1986. "The shikimic acid pathway". (Volume 20 in the series "Recent advances in phytochemistry"). Plenum Press, New York.

Davies, G. M., K. J. Barrett-Bee, D. A. Jude, M. Lehan, W. W. Nichols, P. E. Pinder, J. L. Thain, W. J. Watkins, and R. G. Wilson. 1994. (6S)-6-fluoroshikimic acid, an antibacterial agent acting on the aromatic biosynthetic pathway. Antimicrob. Agents Chemother. 38: 403-406.

Davis, B. D., and E. S. Mingioli. 1953. Aromatic biosynthesis. VII. Accumulation of two derivatives of shikimic acid by bacterial mutants. J. Bacteriol. 66: 129-136.

De Clercq, E. 2002. Strategies in the design of antiviral drugs. Nature Reviews/Drug Discovery 1: 13-25.

Dell, K. A., and J. W. Frost. 1993. Identification and removal of impediments to biocatalytic synthesis of aromatics from D-glucose: Rate-limiting enzymes in the common aromatic pathway of aromatic amino acid biosynthesis. J. Am. Chem. Soc. 115: 11581-11589.

Farina, V., and J. D. Brown. 2006. Tamiflu: The supply problem. Angew. Chem. Int. Ed. 45: 7330-7334.

Federspiel, M., R. Fischer, M. Hennig, H.-J. Mair, T. Oberhauser, G. Rimmler, T. Albiez, J. Bruhin, H. Estermann, C. Gandert, V. Gockel, S. Gotzo, U. Hoffmann, G. Huber, G. Janatsch, S. Lauper, O. Rockel-Stabler, R. Trussardi, and A. G. Zwahlen. 1999. Industrial synthesis of the key precursor in the synthesis of the anti-influenza drug oseltamivir phosphate (Ro 64-0796/002, GS-4104-02): Ethyl (3R,4S,5S)-4,5-epoxy-3-(1-ethyl-propoxy)-cyclohex-1-ene-1-carboxylate. Organic Process Research and Development 3: 266-274.

Fischer, R. S., A. Berry, C. G. Gaines, and R. A. Jensen. 1986. Comparative action of glyphosate as a trigger of energy drain in eubacteria. J. Bacteriol. 168: 1147-1154.

Fotheringham, I. G., and J. Nelms. DNA encoding pheA feedback inhibition resistant enzyme analogs. U.S. Pat. No. 5,120,837.

Fotheringham, I. G., and J. Nelms. Methods and materials for pheA feedback inhibition resistance. European Patent 0418840 B1.

Franz, J. E., M. K. Mao, and J. A. Sikorski. 1997. "Glyphosate. A unique global herbicide". American Chemical Society Monograph 189. American Chemical Society, Washington, D.C.

Frost, J. W. Enhanced production of common aromatic pathway compounds. U.S. Pat. No. 5,168,056

Frost, J. W., K. M. Frost, and D. R. Knop. Biocatalytic synthesis of shikimic acid. International Publication No. WO 00/44923.

Frost, J. W., K. M. Frost, and D. R. Knop. Biocatalytic synthesis of shikimic acid. International Publication No. WO 02/29078.

Frost, J. W., K. M. Frost, and D. R. Knop. Biocatalytic synthesis of shikimic acid. U.S. Pat. No. 6,472,169.

Frost, J. W., K. M. Frost, and D. R. Knop. Biocatalytic synthesis of shikimic acid. U.S. Pat. No. 6,613,552.

Frost, J. W., K. D. Snell, and K. M. Frost. Deblocking the common pathway of aromatic amino acid synthesis. U.S. Pat. No. 5,776,736.

Frost, J. W., K. D. Snell, and K. M. Frost. Deblocking the common pathway of aromatic amino acid synthesis. European Patent EP 0763127 B1.

Fukuta, Y., T. Mita, N. Fukuda, M. Kanai, and M. Shibasaki. 2006. De novo synthesis of Tamiflu via a catalytic asymmetric ring-opening of meso-aziridines with TMSN3. J. Am. Chem. Soc. 128: 6312-6313.

Garner, C., and K. M. Herrmann. 1983. Biosynthesis of phenylalanine. In Herrmann, K. M., and R. L. Somerville (ed.) "Amino acids: Biosynthesis and genetic regulation" pp. 323-338. Addison-Wesley Publishing Co., Reading, Mass.

Grossbard, E., and D. Atkinson. 1985. "The herbicide glyphosate". Butterworths, London.

Harring, T., J. C. Streibig, and S. Husted. 1998. Accumulation of shikimic acid: A technique for screening glyphosate efficacy. J. Agric. Food Chem. 46: 4406-4412.

Haslam, E. 1974. "The shikimate pathway". John Wiley and Sons, New York.

Haslam, E. 1993. "Shikimic acid. Metabolism and metabolites." John Wiley and Sons, Chichester, England.

Hasunuma, K., and M. Sekiguchi. 1977. Replication of plasmid pSC101 in Escherichia coli $K_{12}$: Requirement for dnaA function. Molec. Gen. Genet. 154: 225-230.

Henry, W. B., D. L. Shaner, and M. S. West. 2007. Shikimate accumulation in sunflower, wheat, and proso millet after glyphosate application. Weed Science 55: 1-5.

Herrmann, K. M. 1983. The common aromatic biosynthetic pathway. In Herrmann, K. M., and R. L. Somerville (ed.) "Amino acids: Biosynthesis and genetic regulation" pp. 301-322. Addison-Wesley Publishing Co., Reading, Mass.

Herrmann, K. M. 1995a. The shikimate pathway: Early steps in the biosynthesis of aromatic compounds. The Plant Cell 7: 907-919.

Herrmann, K. M. 1995b. The shikimate pathway as an entry to aromatic secondary metabolism. Plant Physiol. 107: 7-12.

Herrmann, K. M., and L. M. Weaver. 1999. The shikimate pathway. Ann. Rev. Plant. Physiol. Plant Mol. Biol. 50: 473-503.

Ikeda, M. 2003. Amino acid production processes. In Faurie, R., and J. Thommel (ed.) "Vol. 79 in Advances in biochemical engineering biotechnology. Microbial production of amino acids." pp. 1-35. Springer-Verlag, Berlin.

Iomantas, Y. A. V., E. G. Abalakina, B. M. Polanuer, T. A. Yampolskaya, T. A. Bachina, and Y. I. Kozlov. Method for producing shikimic acid. U.S. Pat. No. 6,436,664.

Johansson, L. 2006. Metabolic analysis of shikimic acid producing Escherichia coli. PhD thesis, Lund University, Sweden.

Johansson, L., and G. Liden. 2006. Transcriptome analysis of a shikimic acid producing strain of Escherichia coli W3110 grown under carbon- and phosphate-limited conditions. J. Biotechnol. 126: 528-545.

Johansson, L., A. Lindskog, G. Silfversparre, C. Cimander, K. F. Nielsen, and G. Liden. 2005. Shikimic acid production by a modified strain of E. coli (W3110.shik1) under phosphate-limited and carbon-limited conditions. Biotechnol. Bioeng. 92: 541-552.

Kim, C. U., W. Lew, M. A. Williams, H. Liu, L. Zhang, S. Swaminathan, N. Bischofberger, M. S. Chen, D. B. Mendel, C. Y. Tai, W. G. Layer, and R. C. Stevens. 1997. Influenza neuraminidase inhibitors possessing a novel hydrophobic interaction in the enzyme active site: Design, synthesis, and structural analysis of carbocyclic sialic acid analogues with potent anti-influenza activity. J. Am. Chem. Soc. 119: 681-690.

Kim, C. U., W. Lew, M. A. Williams, H. Wu, L. Zhang, X. Chen, P. A. Escarpe, D. B. Mendel, W. G. Layer, and R. C. Stevens. 1998. Structure-activity relationship studies of novel carbocyclic influenza neuraminidase inhibitors. J. Am. Chem. Soc. 41: 2451-2460.

Knop, D. R., K. M. Draths, S. S. Chandran, J. L. Barker, R. von Daeniken, W. Weber, and J. W. Frost. 2001. Hydroaromatic equilibration during biosynthesis of shikimic acid. J. Am. Chem. Soc. 123: 10173-10182.

Kramer, M., J. Bongaerts, R. Bovenberg, S. Kremer, U. Muller, S. Orf, M. Wubbolts, and L. Raeven. 2003. Metabolic engineering for microbial production of shikimic acid. Metabolic Engineering 5: 277-283.

Khudyakov, Y. E., and H. A. Fields. 2003. "Artificial DNA: Methods and applications". CRC Press, Boca Raton, Fla.

Lew, W., C. U. Kim, H. Liu, and M. A. Williams. Carbocyclic compounds. U.S. Pat. No. 5,866,601.

Malmberg, M., and B. Westrup. Process for the isolation of polyhydroxy cyclic carboxylic acids. U.S. Pat. No. 6,794,164.

McConkey, G. A. 1999. Targeting the shikimate pathway in the malaria parasite Plasmodium falciparum. Antimicrob. Agents Chemother. 43: 175-177.

Mueller, T. C., J. H. Massey, R. M. Hayes, C. L. Main, and C. N. Stewart. 2003. Shikimate accumulates in both glyphosate-sensitive and glyphosate-resistant horseweed (Conyza canadensis L. Cronq.). J. Agric. Food Chem. 51: 680-684.

Nelms, J., R. M. Edwards, J. Warwick, and I. Fotheringham. 1992. Novel mutations in the pheA gene of Escherichia coli K-12 which result in highly feedback inhibition-resistant variants of chorismate mutase/prephenate dehydrogenase. Appl. Environ. Microbiol. 58: 2592-2598.

Payne, R., and M. Edmonds. 2005. Isolation of shikimic acid from star aniseed. J. Chem. Ed. 82: 599-600.

Pittard, A. J. 1987. Biosynthesis of the aromatic amino acids, p. 368-394. In Neidhardt, F. C., J. L. Ingraham, K. B. Low, B. Magasanik, M. Schaechter, and H. E. Umbarger (ed.) "*Escherichia coli* and *Salmonella*: Cellular and molecular biology". American Society for Microbiology Press, Washington, D.C.

Pittard, A. J. 1996. Biosynthesis of the aromatic amino acids, p. 458-484. In Neidhardt, F. C., R. Curtiss, J. L. Ingraham, E. C. C. Lin, K. B. Low, B. Magasanik, W. S. Reznikoff, M. Riley, M. Schaechter, and H. E. Umbarger (ed.) "*Escherichia coli* and *Salmonella*: Cellular and molecular biology". American Society for Microbiology Press, Washington, D.C.

Pline, W. A., J. W. Wilcut, S. O. Duke, K. L. Edmisten, and R. Wells. 2002. Tolerance and accumulation of shikimic acid in response to glyphosate applications in glyphosate—resistant and nonglyphosate-resistant cotton (*Gossypium hirsutum* L.). J. Agric. Food Chem. 50: 506-512.

Polen, T., M. Kramer, J. Bongaerts, M. Wubbolts, and V. F. Wendisch. 2005. The global gene expression response of *Escherichia coli* to L-phenylalanine. J. Biotechnol. 115: 221-237.

Pouwels, P. H., B. E. Enger-Valk, and W. J. Brammar 1985. "Cloning vectors. A laboratory manual". Elsevier Science Publishers, Amsterdam.

Roberts, F., C. W. Roberts, J. J. Johnson, D. E. Kyle, T. Krell, J. R. Coggins, G. H. Coombs, W. K. Milhous, S. Tzipori, D. J. P. Ferguson, D. Chakrabarti, and R. McLeod. 1998. Evidence for the shikimate pathway in apicomplexan parasites. Nature 393: 801-805.

Roberts, C. W., F. Roberts, R. E. Lyons, M. J. Kiristis, E. J. Mui, J. Finnerty, J. J. Johnson, D. J. P. Ferguson, J. R. Coggins, T. Krell, G. H. Coombs, W. K. Milhous, D. E. Kyle, S. Tzipori, J. Barnwell, J. B. Dame, J. Carlton, and R. McLeod. 2002. The shikimate pathway and its branches in apicomplexan parasites. J. Infect. Dis. 185 (Suppl. 1): S25-36.

Rodriguez, R. L., and D. T. Denhardt. 1988. "Vectors. A survey of molecular cloning vectors and their uses". Butterworths, Boston, Mass.

Rohloff, J. C., K. M. Kent, M. J. Postich, M. W. Becker, H. H. Chapman, D. E. Kelly, W. Lew, M. S. Louie, L. R. McGee, E. J. Prisbe, L. M. Schultze, R. H. Yu, and L. Zhang. 1998. Practical total synthesis of the anti-influenza drug GS-4104. J. Org. Chem. 63: 4545-4550.

Sadaka, M., and A. Garcia. 1999. Extraction of shikimic and quinic acids. Chem. Eng. Commun 173: 91-102.

Sambrook, J., and D. W. Russell. 2001. "Molecular cloning. A laboratory manual". Third Edition. Cold Spring Harbor Laboratory Press, Cold Spring Harbor, N.Y.

Shirai, M., R. Miyata, S. Sasaki, K. Sakamoto, S. Yahanda, K. Shibayama, T. Yonehara, and K. Ogawa. Microorganism belonging to the genus *Citrobacter* and process for producing shikimic acid. European Patent Application EP 1092766 A1.

Sprenger, G., R. Siewe, H. Sahm, M. Karutz, and T. Sonke. Microbial preparation of substances from aromatic metabolism. U.S. Pat. No. 6,316,232.

Starcevic, A., S. Akthar, W. C. Dunlap, J. M. Shick, D. Hranueli, J. Cullum, and P. F. Long. 2008. Enzymes of the shikimic acid pathway encoded in the genome of a basal metazoan, Nematostella vectensis, have microbial origins. Proc. Natl. Acad. Sci. 105: 2533-2537.

Steinrucken, H. C., and N. Amrhein. 1980. The herbicide glyphosate is a potent inhibitor of 5-enolpyruvyl-shikimic acid-3-phosphate synthase. Biochem. Biophys. Res. Commun. 94: 1207-1212.

Steinrucken, H. C., and N. Amrhein. 1984. 5-enolpyruvylshikimate-3-phosphate synthase of Klebsiella pneumoniae. 2 Inhibition by glyphosate [N-(phosphonomethyl)glycine]. Eur. J. Biochem. 143: 351-357.

Stryer, L. 1995. "Biochemistry" Fourth Edition. W.H. Freeman and Company, New York.

Tan, D. S., M. A. Foley, B. R. Stockwell, M. D. Shair, and S. L. Schreiber. 1999. Synthesis and preliminary evaluation of a library of polycyclic small molecules for use in chemical genetic assays. J. Am. Chem. Soc. 121: 9073-9087.

Van der Does, T., J. Booij, E. E. Kers, E. J. A. M. Leenderts, M. Sibeijn, and V. Agayn. Process for the recovery of shikimic acid. International Publication No. WO 02/06203.

Vogel, H. J., and D. M. Bonner. 1956. Acetylornithinase of *Escherichia coli*: Partial purification and some properties. J. Biol. Chem. 218: 97-106.

Wanner, B. L. 1996. Phosphorus assimilation and control of the phosphate regulon, p. 1357-1381. In Neidhardt, F. C., R. Curtiss, J. L. Ingraham, E. C. C. Lin, K. B. Low, B. Magasanik, W. S. Reznikoff, M. Riley, M. Schaechter, and H. E. Umbarger (ed.) "*Escherichia coli* and *Salmonella*: Cellular and molecular biology". American Society for Microbiology Press, Washington, D.C.

Weiss, U., and J. M. Edwards. 1980. "The biosynthesis of aromatic compounds". John Wiley and Sons, New York.

Yeung, Y.-Y., S. Hong, and E. J. Corey. 2006. A short enantioselective pathway for the synthesis of the anti-influenza neuraminidase inhibitor oseltamivir from 1,3-butadiene and acrylic acid. J. Am. Chem. Soc. 128: 6310-6311.

---

What is claimed is:

1. A method for producing shikimic acid comprising:
   a) contacting a microorganism having a deregulated common aromatic biosynthetic pathway with glyphosate whereby synthesis of shikimate-3-phosphate is increased, and growing the microorganism in a minimal culture medium wherein the minimal culture medium as formulated is phosphate limiting or phosphate-free; and
   b) converting the shikimate-3-phosphate to shikimic acid, wherein the conversion comprises increasing the temperature and/or reducing the pH of the minimal culture medium as compared to the temperature and/or pH conditions at which the microorganism is grown in step a).

2. The method of claim 1 wherein the microorganism is a bacterium.

3. The method of claim 2 wherein the bacterium is a strain of *Escherichia coli*.

4. The method of claim 3 wherein the strain of *Escherichia coli* is strain LBB427.

5. The method of claim 4 wherein the strain of *Escherichia coli* is strain LBB427 transformed with the plasmid pXT1457.

6. The method of claim 4 wherein the strain of *Escherichia coli* is strain LBB427 transformed with the plasmid pXT1483.

7. The method of claim 1 wherein the conversion of shikimate-3-phosphate to shikimic acid further comprises conversion by a phosphatase enzyme.

8. The method of claim 7 wherein the phosphatase enzyme is alkaline phosphatase.

9. The method of claim 1 wherein the deregulated common aromatic biosynthetic pathway of the microorganism comprises deregulated biosynthesis of one or more compounds selected from the group consisting of tryptophan, phenylalanine, tyrosine, shikimic acid, shikimate-3-phosphate, 5-enolpyruvoylshikimate-3-phosphate, chorismic acid, para hydroxybenzoic acid, para-aminobenzoic acid, 2,3-dihydroxybenzoic acid, folate, ubiquinone, menaquinone, and enterochelin.

10. The method of claim 9 wherein the deregulated common aromatic biosynthetic pathway of the microorganism comprises deregulated biosynthesis of phenylalanine.

11. The method of claim 1 wherein the method further comprises deregulating the microorganism's common aromatic biosynthetic pathway.

12. The method of claim 1 wherein the method further comprises isolating the shikimic acid.

13. A method for synthesizing a chemical compound, wherein the synthesized compound is 6-fluoroshikimic acid, oseltamivir, or oseltamivir phosphate, the method comprising
   a) producing shikimic acid according to claim 1; and
   b) synthesizing the chemical compound using the shikimic acid as a reagent in the synthesis.

\* \* \* \* \*

SEQUENCE LISTING

```
<160> NUMBER OF SEQ ID NOS: 5

<210> SEQ ID NO 1
<211> LENGTH: 1235
<212> TYPE: DNA
<213> ORGANISM: Artificial sequence
<220> FEATURE:
<223> OTHER INFORMATION: Nucleotide sequence of the synthetic
      EcoRI-BamHI restriction fragment carried on the plasmids pXT1457
      and pXT1483.

<400> SEQUENCE: 1
gaattctttt ttgttgacag cgtgaaaaca gtacgggtat aatactaaag tcacaaaaag      60
```

-continued

```
gcaacactat gacatcggaa aacccgttac tggcgctgcg agagaaaatc agcgcgctgg    120
atgaaaaatt attagcgtta ctggcagaac ggcgcgaact ggccgtcgag gtgggaaaag    180
ccaaactgct ctcgcatcgc ccggtacgtg atattgatcg tgaacgcgat ttgctggaaa    240
gattaattac gctcggtaaa gcgcaccatc tggacgccca ttacattact cgcctgttcc    300
agctcatcat tgaagattcc gtattaactc agcaggcttt gctccaacaa catctcaata    360
aaattaatcc gcactcagca cgcatcgctt ttctcggccc caaaggttct tattcccatc    420
ttgcggcgcg ccagtatgct gcccgtcact ttgagcaatt cattgaaagt ggctgcgcca    480
aatttgccga tattttaat caggtggaaa ccggccaggc cgactatgcc gtcgtaccga    540
ttgaaaatac cagctccggt gccataaacg acgtttacga tctgctgcaa cataccagct    600
tgtcgattgt tggcgagatg acgttaacta tcgaccattg tttgttggtc tccggcacta    660
ctgatttatc caccatcaat acggtctaca gccatccgca gccattccag caatgcagca    720
aattccttaa tcgttatccg cactggaaga ttgaatatac cgaaagtacg tctgcggcaa    780
tggaaaaggt tgcacaggca aaatcaccgc atgttgctgc gttgggaagc gaagctggcg    840
gcactttgta cggtttgcag gtactggagc gtattgaagc aaatcagcga caaaacttca    900
cccgatttgt ggtgttggcg cgtaaagcca ttaacgtgtc tgatcaggtt ccggcgaaaa    960
ccacgttgtt aatggcgaaa caagccggtg cgctggttga agcgttgctg gtactgcgca   1020
accacaatct gattatgacc cgtctggaat cacgcccgat tcacggtaat ccatgggaag   1080
agatgttcta tctggatatt caggccaatc ttgaatcagc ggaaatgcaa aaagcattga   1140
aagagttagg ggaaatcacc cgttcaatga aggtattggg ctgttaccca agtgagaacg   1200
tagtgcctgt tgatccaacc tgatgaaaag gatcc                               1235
```

<210> SEQ ID NO 2
<211> LENGTH: 384
<212> TYPE: PRT
<213> ORGANISM: Escherichia coli

<400> SEQUENCE: 2

```
Met Thr Ser Glu Asn Pro Leu Ala Leu Arg Glu Lys Ile Ser Ala
1               5                   10                  15

Leu Asp Glu Lys Leu Leu Ala Leu Leu Ala Glu Arg Arg Glu Leu Ala
            20                  25                  30

Val Glu Val Gly Lys Ala Lys Leu Leu Ser His Arg Pro Val Arg Asp
        35                  40                  45

Ile Asp Arg Glu Arg Asp Leu Leu Glu Arg Leu Ile Thr Leu Gly Lys
    50                  55                  60

Ala His His Leu Asp Ala His Tyr Ile Thr Arg Leu Phe Gln Leu Ile
65                  70                  75                  80

Ile Glu Asp Ser Val Leu Thr Gln Gln Ala Leu Leu Gln Gln His Leu
                85                  90                  95

Asn Lys Ile Asn Pro His Ser Ala Arg Ile Ala Phe Leu Gly Pro Lys
            100                 105                 110

Gly Ser Tyr Ser His Leu Ala Ala Arg Gln Tyr Ala Ala Arg His Phe
        115                 120                 125

Glu Gln Phe Ile Glu Ser Gly Cys Ala Lys Phe Ala Asp Ile Phe Asn
    130                 135                 140

Gln Val Glu Thr Gly Gln Ala Asp Tyr Ala Val Val Pro Ile Glu Asn
145                 150                 155                 160

Thr Ser Ser Gly Ala Ile Asn Asp Val Tyr Asp Leu Leu Gln His Thr
                165                 170                 175
```

```
Ser Leu Ser Ile Val Gly Glu Met Thr Leu Thr Ile Asp His Cys Leu
        180                 185                 190

Leu Val Ser Gly Thr Thr Asp Leu Ser Thr Ile Asn Thr Val Tyr Ser
        195                 200                 205

His Pro Gln Pro Phe Gln Gln Cys Ser Lys Phe Leu Asn Arg Tyr Pro
210                 215                 220

His Trp Lys Ile Glu Tyr Thr Glu Ser Thr Ser Ala Ala Met Glu Lys
225                 230                 235                 240

Val Ala Gln Ala Lys Ser Pro His Val Ala Ala Leu Gly Ser Glu Ala
                245                 250                 255

Gly Gly Thr Leu Tyr Gly Leu Gln Val Leu Glu Arg Ile Glu Ala Asn
            260                 265                 270

Gln Arg Gln Asn Phe Thr Arg Phe Val Val Leu Ala Arg Lys Ala Ile
        275                 280                 285

Asn Val Ser Asp Gln Val Pro Ala Lys Thr Thr Leu Leu Met Ala Lys
290                 295                 300

Gln Ala Gly Ala Leu Val Glu Ala Leu Leu Val Leu Arg Asn His Asn
305                 310                 315                 320

Leu Ile Met Thr Arg Leu Glu Ser Arg Pro Ile His Gly Asn Pro Trp
                325                 330                 335

Glu Glu Met Phe Tyr Leu Asp Ile Gln Ala Asn Leu Gly Ser Ala Glu
            340                 345                 350

Met Gln Lys Ala Leu Lys Glu Leu Gly Glu Ile Thr Arg Ser Met Lys
        355                 360                 365

Val Leu Gly Cys Tyr Pro Ser Glu Asn Val Val Pro Val Asp Pro Thr
370                 375                 380
```

<210> SEQ ID NO 3
<211> LENGTH: 6198
<212> TYPE: DNA
<213> ORGANISM: Artificial sequence
<220> FEATURE:
<223> OTHER INFORMATION: Nucleotide sequence of the plasmid pXT1483.

<400> SEQUENCE: 3

```
gaattctttt tgttgacag cgtgaaaaca gtacgggtat aatactaaag tcacaaaaag    60
gcaacactat gacatcggaa aacccgttac tggcgctgcg agagaaaatc agcgcgctgg   120
atgaaaaatt attagcgtta ctggcagaac ggcgcgaact ggccgtcgag gtgggaaaag   180
ccaaactgct ctcgcatcgc ccggtacgtg atattgatcg tgaacgcgat ttgctggaaa   240
gattaattac gctcggtaaa gcgcaccatc tggacgccca ttacattact cgcctgttcc   300
agctcatcat tgaagattcc gtattaactc agcaggcttt gctccaacaa catctcaata   360
aaattaatcc gcactcagca cgcatcgctt ttctcggccc caaaggttct tattcccatc   420
ttgcggcgcg ccagtatgct gcccgtcact tgagcaatt cattgaaagt ggctgcgcca   480
aatttgccga tatttttaat caggtggaaa ccggccaggc cgactatgcc gtcgtaccga   540
ttgaaaatac cagctccggt gccataaacg acgtttacga tctgctgcaa cataccagct   600
tgtcgattgt tggcgagatg acgttaacta tcgaccattg tttgttggtc tccggcacta   660
ctgatttatc caccatcaat acggtctaca gccatccgca gccattccag caatgcagca   720
aattccttaa tcgttatccg cactggaaga ttgaatatac gaaagtacg tctgcggcaa   780
tggaaaaggt tgcacaggca aaatcaccgc atgttgctgc gttgggaagc gaagctggcg   840
gcactttgta cggtttgcag gtactggagc gtattgaagc aaatcagcga caaaacttca   900
```

```
cccgatttgt ggtgttggcg cgtaaagcca ttaacgtgtc tgatcaggtt ccggcgaaaa    960
ccacgttgtt aatggcgaaa caagccggtg cgctggttga agcgttgctg gtactgcgca   1020
accacaatct gattatgacc cgtctggaat cacgcccgat tcacggtaat ccatgggaag   1080
agatgttcta tctggatatt caggccaatc ttgaatcagc ggaaatgcaa aaagcattga   1140
aagagttagg ggaaatcacc cgttcaatga aggtattggg ctgttaccca agtgagaacg   1200
tagtgcctgt tgatccaacc tgatgaaaag gatcctctac gccggacgca tcgtggccgg   1260
catcaccggc gccacaggtg cggttgctgg cgcctatatc gccgacatca ccgatgggga   1320
agatcgggct cgccacttcg ggctcatgag cgcttgtttc ggcgtgggta tggtggcagg   1380
ccccgtggcc gggggactgt tgggcgccat ctccttgcat gcaccattcc ttgcggcggc   1440
ggtgctcaac ggcctcaacc tactactggg ctgcttccta atgcaggagt cgcataaggg   1500
agagcgtcga ccgatgccct tgagagcctt caacccagtc agctccttcc ggtgggcgcg   1560
gggcatgact atcgtcgccg cacttatgac tgtcttcttt atcatgcaac tcgtaggaca   1620
ggtgccggca gcgctctggg tcattttcgg cgaggaccgc tttcgctgga gcgcgacgat   1680
gatcggcctg tcgcttgcgg tattcggaat cttgcacgcc ctcgctcaag ccttcgtcac   1740
tggtcccgcc accaaacgtt tcggcgagaa gcaggccatt atcgccggca tggcggccga   1800
cgcgctgggc tacgtcttgc tggcgttcgc gacgcgaggc tggatggcct tccccattat   1860
gattcttctc gcttccggcg gcatcgggat gcccgcgttg caggccatgc tgtccaggca   1920
ggtagatgac gaccatcagg gacagcttca aggatcgctc gcggctctta ccagcctaac   1980
ttcgatcatt ggaccgctga tcgtcacggc gatttatgcc gcctcggcga gcacatggaa   2040
cgggttggca tggattgtag gcgccgcct ataccttgtc tgcctccccg cgttgcgtcg   2100
cggtgcatgg agcgggcca cctcgacctg aatggaagcc ggcggcacct cgctaacgga   2160
ttcaccactc caagaattgg agccaatcaa ttcttgcgga gaactgtgaa tgcgcaaacc   2220
aacccttggc agaacatatc catcgcgtcc gccatctcca gcagccgcac gcggcgcatc   2280
tcgggcagcg ttgggtcctg gccacggtg cgcatgatcg tgctcctgtc gttgaggacc   2340
cggctaggct ggcggggttg ccttactggt tagcagaatg aatcaccgat acgcgagcga   2400
acgtgaagcg actgctgctg caaaacgtct gcgacctgag caacaacatg aatggtcttc   2460
ggtttccgtg tttcgtaaag tctggaaacg cggaagtcag cgccctgcac cattatgttc   2520
cggatctgca tcgcaggatg ctgctggcta ccctgtggaa cacctacatc tgtattaacg   2580
aagcgctggc attgaccctg agtgattttt ctctggtaga tctatgcatc gtgaccatgc   2640
tctgtaccag tctgccggat tgcttatcct ggcgggtctg gttgacagta agacgggtaa   2700
gcctgttgat gataccgctg ccttactggg tgcattagcc agtctgaatg acctgtcacg   2760
ggataatccg aagtggtcag actggaaaat cagagggcag gaactgctga acagcaaaaa   2820
gtcagatagc accacatagc agacccgcca taaaacgccc tgagaagccc gtgacgggct   2880
tttcttgtat tatgggtagt ttccttgcat gaatccataa aaggcgcctg tagtgccatt   2940
tacccccatt cactgccaga gccgtgagcg cagcgaactg aatgtcacga aaaagacagc   3000
gactcaggtg cctgatggtc ggagacaaaa ggaatattca gcgatttgcc cgagcttgcg   3060
agggtgctac ttaagccttt agggttttaa ggtctgtttt gtagaggagc aaacagcgtt   3120
tgcgacatcc ttttgtaata ctgcggaact gactaaagta gtgagttata cacagggctg   3180
ggatctattc ttttatctt ttttattct ttctttattc tataaattat aaccacttga   3240
atataaacaa aaaaaacaca caaggtcta gcggaattta cagagggtct agcagaattt   3300
```

```
acaagttttc cagcaaaggt ctagcagaat ttacagatac ccacaactca aggaaaagg    3360 actagtaatt atcattgact agcccatctc aattggtata gtgattaaaa tcacctagac    3420
caattgagat gtatgtctga attagttgtt ttcaaagcaa atgaactagc gattagtcgc    3480
tatgacttaa cggagcatga aaccaagcta attttatgct gtgtggcact actcaacccc    3540
acgattgaaa accctacaag gaaagaacgg acggtatcgt tcacttataa ccaatacgct    3600
cagatgatga acatcagtag ggaaaatgct tatggtgtat tagctaaagc aaccagagag    3660
ctgatgacga gaactgtgga aatcaggaat cctttggtta aaggctttga gattttccag    3720
tggacaaact atgccaagtt ctcaagcgaa aaattagaat tagttttag tgaagagata    3780 ttgccttatc ttttccagtt aaaaaaattc ataaaatata atctggaaca tgttaagtct    3840
tttgaaaaca aatactctat gaggatttat gagtggttat taaaagaact aacacaaaag    3900
aaaactcaca aggcaaatat agagattagc cttgatgaat ttaagttcat gttaatgctt    3960
gaaaataact accatgagtt taaaaggctt aaccatgggg ttttgaaacc aataagtaaa    4020
gatttaaaca cttacagcaa tatgaaattg gtggttgata agcgaggccg cccgactgat    4080
acgttgattt tccaagttga actagataga caaatggatc tcgtaaccga acttgagaac    4140
aaccagataa aaatgaatgg tgacaaaata ccaacaacca ttacatcaga ttcctaccta    4200
cataacggac taagaaaaac actacacgat gctttaactg caaaaattca gctcaccagt    4260
tttgaggcaa aattttgag tgacatgcaa agtaagtatg atctcaatgg ttcgttctca    4320
tggctcacgc aaaaacaacg aaccacacta gagaacatac tggctaaata cggaaggatc    4380
tgaggttctt atggctcttg tatctatcag tgaagcatca agactaacaa acaaaagtag    4440
aacaactgtt caccgttaca tatcaaaggg aaaactgtcc atatgcacag atgaaaacgg    4500
tgtaaaaaag atagatacat cagagctttt acgagttttt ggtgcattca aagctgttca    4560
ccatgaacag atcgacaatg taacagatga acagcatgta acacctaata gaacaggtga    4620
aaccagtaaa acaaagcaac tagaacatga aattgaacac ctgagacaac ttgttacagc    4680
tcaacagtca cacatagaca gcctgaaaca ggcgatgctg cttatcgaat caaagctgcc    4740
gacaacacgg gagccagtga cgcctcccgt ggggaaaaaa tcatggcaat tctggaagaa    4800
atagcgcttt cagccggcaa accggctgaa gccggatctg cgattctgat aacaaactag    4860
caacaccaga acagcccgtt tgcgggcagc aaaacccgta cttttggacg ttccggcggt    4920 ttttgtggc gagtggtgtt cgggcggtgc gcgcaagatc cattatggag ctcactagta    4980
gatctggggt ctgacgctca gtggaacgaa aactcacgtt aagggatttt ggtcatgaga    5040
ttatcaaaaa ggatcttcac ctagatcctt ttaaattaaa aatgaagttt taaatcaatc    5100
taaagtatat atgagtaaac ttggtctgac agttaccaat gcttaatcag tgaggcacct    5160
atctcagcga tctgtctatt tcgttcatcc atagttgcct gactccccgt cgtgtagata    5220
actacgatac gggagggctt accatctggc cccagtgctg caatgatacc gcgagaccca    5280
cgctcaccgg ctccagattt atcagcaata aaccagccag ccggaagggc cgagcgcaga    5340
agtggtcctg caactttatc cgcctccatc cagtctatta attgttgccg ggaagctaga    5400
gtaagtagtt cgccagttaa tagtttgcgc aacgttgttg ccattgctgc aggcatcgtg    5460
gtgtcacgct cgtcgtttgg tatggcttca ttcagctccg gttcccaacg atcaaggcga    5520
gttacatgat ccccccatgtt gtgcaaaaaa gcggttagct ccttcggtcc tccgatcgtt    5580
gtcagaagta agttggccgc agtgttatca ctcatggtta tggcagcact gcataattct    5640
cttactgtca tgccatccgt aagatgcttt tctgtgactg gtgagtactc aaccaagtca    5700
```

```
ttctgagaat agtgtatgcg gcgaccgagt tgctcttgcc cggcgtcaac acgggataat    5760
accgcgccac atagcagaac tttaaaagtg ctcatcattg gaaaacgttc ttcggggcga    5820
aaactctcaa ggatcttacc gctgttgaga tccagttcga tgtaacccac tcgtgcaccc    5880
aactgatctt cagcatcttt tactttcacc agcgtttctg ggtgagcaaa aacaggaagg    5940
caaaatgccg caaaaaggg aataagggcg acacggaaat gttgaatact catactcttc    6000
ctttttcaat attattgaag catttatcag ggttattgtc tcatgagcgg atacatattt    6060
gaatgtattt agaaaaataa acaaataggg gttccgcgca catttccccg aaaagtgcca    6120
cctgacgtct aagaaaccat tattatcatg acattaacct ataaaaatag gcgtatcacg    6180
aggccctttc gtcttcaa                                                  6198

<210> SEQ ID NO 4
<211> LENGTH: 217
<212> TYPE: DNA
<213> ORGANISM: Escherichia coli
<220> FEATURE:
<221> NAME/KEY: CDS
<222> LOCATION: (69)..(116)
<220> FEATURE:
<221> NAME/KEY: CDS
<222> LOCATION: (215)..(217)

<400> SEQUENCE: 4
gaattctttt ttgttgacag cgtgaaaaca gtacgggtac tgtactaaag tcacttaagg    60 aaacaaac atg aaa cac ata ccg ttt ttc ttc gca ttc ttt ttt acc ttc   110
        Met Lys His Ile Pro Phe Phe Phe Ala Phe Phe Phe Thr Phe
          1               5                  10 ccc tga atgggaggcg tttcgtcgtg tgaaacagaa tgcgaagacg aacaataagg    166
Pro
15 cctcccaaat cggggggcct tttttattga taacaaaaag gcaacact atg            217
                                                        Met <210> SEQ ID NO 5
<211> LENGTH: 15
<212> TYPE: PRT
<213> ORGANISM: Escherichia coli

<400> SEQUENCE: 5

Met Lys His Ile Pro Phe Phe Phe Ala Phe Phe Phe Thr Phe Pro
  1               5                  10                  15
```